(12) United States Patent
Ludwig et al.

(10) Patent No.: US 10,675,188 B2
(45) Date of Patent: Jun. 9, 2020

(54) CONFIGURABLE ABSORBENT ARTICLES

(71) Applicant: The Procter & Gamble Company, Cincinnati, OH (US)

(72) Inventors: Susan Joy Ludwig, West Chester, OH (US); Amy Lynn Tally, Cold Spring, KY (US); George Christopher Dobrin, Madeira, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 533 days.

(21) Appl. No.: 15/440,012

(22) Filed: Feb. 23, 2017

(65) Prior Publication Data
US 2017/0246043 A1    Aug. 31, 2017

Related U.S. Application Data

(60) Provisional application No. 62/351,325, filed on Jun. 17, 2016, provisional application No. 62/299,794, filed on Feb. 25, 2016.

(51) Int. Cl.
*A61F 13/45* (2006.01)
*A61F 13/49* (2006.01)
(Continued)

(52) U.S. Cl.
CPC ........ *A61F 13/45* (2013.01); *A61F 13/15203* (2013.01); *A61F 13/15585* (2013.01);
(Continued)

(58) Field of Classification Search
CPC .. A61F 13/45; A61F 13/49058; A61F 13/493; A61F 13/505; A61F 13/15203;
(Continued)

(56) References Cited

U.S. PATENT DOCUMENTS 4,257,418 A    3/1981    Hessner
4,315,508 A    2/1982    Bolick
(Continued)

FOREIGN PATENT DOCUMENTS

CN    102217995    10/2011
CN    202027809    11/2011
(Continued)

OTHER PUBLICATIONS

U.S. Appl. No. 16/214,255, filed Dec. 10, 2018, Ludwig et al.
(Continued)

*Primary Examiner* — Tatyana Zalukaeva
*Assistant Examiner* — Gabriella E Burnette
(74) *Attorney, Agent, or Firm* — Daniel S. Albrecht

(57) ABSTRACT

Configurable absorbent articles are provided. The absorbent articles may comprise a topsheet, a backsheet, and an absorbent core positioned at least partially intermediate the topsheet and the backsheet. The absorbent articles may comprise a first waist region, a second waist region, a crotch region extending intermediate the first waist region and the second waist region, and an outer cover material joined to the backsheet and forming a portion of a garment-facing surface of the absorbent article. The absorbent articles may comprise a pair of leg cuffs and a fully removable fastening member. The fastening member may comprise a first fastener on a first surface of the fastening member and positioned proximate to a first end and a second fastener on the first surface and positioned proximate to a second end. The absorbent articles may also comprise a wetness guard.

19 Claims, 41 Drawing Sheets

(51) Int. Cl.
| | |
|---|---|
| *A61F 13/493* | (2006.01) |
| *A61F 13/505* | (2006.01) |
| *A61F 13/15* | (2006.01) |
| *A61F 13/56* | (2006.01) |
| *A61F 13/494* | (2006.01) |
| *A61F 13/511* | (2006.01) |
| *A61F 13/513* | (2006.01) |
| *A61F 13/51* | (2006.01) |
| *A61F 13/551* | (2006.01) |
| *A61F 13/514* | (2006.01) |
| *A61F 13/42* | (2006.01) |

(52) U.S. Cl.
CPC ............ *A61F 13/42* (2013.01); *A61F 13/493* (2013.01); *A61F 13/49017* (2013.01); *A61F 13/49058* (2013.01); *A61F 13/49466* (2013.01); *A61F 13/505* (2013.01); *A61F 13/511* (2013.01); *A61F 13/514* (2013.01); *A61F 13/51121* (2013.01); *A61F 13/51394* (2013.01); *A61F 13/52* (2013.01); *A61F 13/55105* (2013.01); *A61F 13/5622* (2013.01); *A61F 13/5638* (2013.01); *A61F 2013/15154* (2013.01); *A61F 2013/4506* (2013.01); *A61F 2013/4512* (2013.01); *A61F 2013/4593* (2013.01); *A61F 2013/49063* (2013.01); *A61F 2013/49074* (2013.01); *A61F 2013/51355* (2013.01)

(58) Field of Classification Search
CPC ................ A61F 13/42; A61F 13/49017; A61F 13/49466; A61F 13/51121; A61F 13/51394; A61F 13/52; A61F 13/15585; A61F 13/511; A61F 2013/4506; 2013/4512; A61F 2013/4593; 2013/49063; A61F 2013/49074; A61F 2013/15154; A61F 2013/51355; 13/514; A61F 13/55105; A61F 13/5638; A61F 13/5622
See application file for complete search history.

(56) References Cited

U.S. PATENT DOCUMENTS

| | | | |
|---|---|---|---|
| 4,661,102 A | 4/1987 | Shikata et al. | |
| 5,026,364 A | 6/1991 | Robertson | |
| H1440 H | 5/1995 | New et al. | |
| 5,653,842 A | 8/1997 | Kuen | |
| 5,702,377 A | 12/1997 | Collier, IV et al. | |
| 5,827,259 A | 10/1998 | Laux et al. | |
| 5,843,066 A | 12/1998 | Dobrin | |
| 5,906,604 A | 5/1999 | Ronnberg et al. | |
| 5,931,827 A | 8/1999 | Buell et al. | |
| 5,934,470 A | 8/1999 | Bauer et al. | |
| 5,938,652 A | 8/1999 | Sauer | |
| 5,941,863 A | 8/1999 | Guidotti et al. | |
| 5,971,970 A | 10/1999 | Carlbark et al. | |
| 5,993,433 A | 11/1999 | St. Louis et al. | |
| 6,010,490 A | 1/2000 | Freeland et al. | |
| 6,010,491 A | 1/2000 | Roe et al. | |
| 6,120,486 A | 9/2000 | Toyoda et al. | |
| 6,132,410 A | 10/2000 | Van Gompel et al. | |
| 6,135,988 A | 10/2000 | Turner et al. | |
| 6,217,563 B1 | 4/2001 | Van Gompel et al. | |
| 6,315,764 B1 | 11/2001 | Faulks et al. | |
| 6,336,922 B1 | 1/2002 | VanGompel et al. | |
| 6,371,950 B1 | 4/2002 | Roslansky et al. | |
| 6,432,099 B2 | 8/2002 | Ronnberg | |
| 6,491,677 B1 | 12/2002 | Glaug et al. | |
| 6,626,880 B2 | 9/2003 | Onishi | |
| 6,627,786 B2 | 9/2003 | Roe et al. | |
| 6,638,262 B2 | 10/2003 | Suzuki et al. | |
| 6,659,993 B2 | 12/2003 | Minato et al. | |
| 6,767,344 B2 | 7/2004 | Suzuki | |
| 6,790,203 B2 | 9/2004 | Een | |
| 6,817,993 B1 | 11/2004 | Simmons et al. | |
| 6,921,394 B2 | 7/2005 | Sayama et al. | |
| 7,118,557 B2 | 10/2006 | Minato et al. | |
| 7,163,530 B1 | 1/2007 | Toyoshima et al. | |
| 7,419,562 B2 | 9/2008 | Van Gompel et al. | |
| 7,753,899 B2 | 7/2010 | Mori et al. | |
| 7,785,309 B2* | 8/2010 | Van Gompel | A61F 13/4942 604/385.01 |
| 7,879,017 B1 | 2/2011 | Tabata et al. | |
| 8,181,278 B2 | 5/2012 | Odorzynski et al. | |
| 8,216,201 B2 | 7/2012 | Beck | |
| 8,231,592 B2 | 7/2012 | Suzuki et al. | |
| 8,430,858 B2 | 4/2013 | Bäck | |
| 8,449,518 B2 | 5/2013 | Allison-Rogers | |
| 8,668,680 B2 | 3/2014 | Ichikawa et al. | |
| 8,747,380 B2 | 6/2014 | Coates | |
| 8,764,721 B2 | 7/2014 | Van Gompel et al. | |
| 8,764,722 B2 | 7/2014 | Rhein et al. | |
| 8,821,467 B1 | 9/2014 | Minella | |
| 8,894,626 B2 | 11/2014 | Beck | |
| 8,926,580 B2 | 1/2015 | Carney et al. | |
| 8,992,496 B2 | 3/2015 | Bäck | |
| 9,044,358 B2 | 6/2015 | Nakajima et al. | |
| 9,168,181 B2 | 10/2015 | Popp et al. | |
| 9,259,362 B2 | 2/2016 | Popp et al. | |
| 9,445,951 B2 | 9/2016 | Moberg-alehammar et al. | |
| 9,554,952 B2 | 1/2017 | Ronnberg et al. | |
| 9,675,503 B2 | 6/2017 | Carney | |
| 2002/0016579 A1 | 2/2002 | Stenberg | |
| 2002/0111596 A1* | 8/2002 | Fletcher | A61F 13/15211 604/385.03 |
| 2002/0120248 A1 | 8/2002 | Onishi et al. | |
| 2002/0138054 A1 | 9/2002 | Erdman et al. | |
| 2003/0050616 A1 | 3/2003 | Reynolds et al. | |
| 2003/0124928 A1 | 7/2003 | Sherrod et al. | |
| 2003/0232556 A1 | 12/2003 | Toro et al. | |
| 2004/0102757 A1 | 5/2004 | Olson | |
| 2004/0127867 A1 | 7/2004 | Odorzynski et al. | |
| 2004/0230171 A1 | 11/2004 | Ando et al. | |
| 2005/0222546 A1 | 10/2005 | Vargo et al. | |
| 2006/0241559 A1* | 10/2006 | Buhrow | A61F 13/493 604/385.09 |
| 2006/0247597 A1 | 11/2006 | Hogan et al. | |
| 2007/0049895 A1 | 3/2007 | Van Gompel et al. | |
| 2007/0233027 A1 | 3/2007 | Roe et al. | |
| 2007/0102750 A1 | 5/2007 | Kim et al. | |
| 2007/0232180 A1 | 10/2007 | Polat et al. | |
| 2008/0065034 A1 | 3/2008 | Vargo et al. | |
| 2008/0082072 A1 | 4/2008 | Helmfridsson et al. | |
| 2010/0004616 A1 | 1/2010 | Nakamura et al. | |
| 2010/0168695 A1 | 7/2010 | Robles et al. | |
| 2010/0234822 A1 | 9/2010 | Back | |
| 2010/0241098 A1 | 9/2010 | Brownlee | |
| 2011/0184372 A1 | 7/2011 | Esping et al. | |
| 2012/0116339 A1* | 5/2012 | Labit | A61F 13/49004 604/372 |
| 2013/0110065 A1 | 5/2013 | Takahashi et al. | |
| 2014/0068839 A1 | 3/2014 | Steele et al. | |
| 2014/0107605 A1 | 4/2014 | Schroer et al. | |
| 2014/0135724 A1 | 5/2014 | Robles et al. | |
| 2014/0142528 A1 | 5/2014 | Wang et al. | |
| 2014/0142529 A1 | 5/2014 | Cheng | |
| 2014/0155856 A1 | 6/2014 | Rönnberg et al. | |
| 2014/0163501 A1 | 6/2014 | Ehrnsperger et al. | |
| 2014/0221956 A1 | 8/2014 | Martynus et al. | |
| 2014/0257227 A1 | 9/2014 | Roe | |
| 2014/0303589 A1 | 10/2014 | Paz et al. | |
| 2014/0345034 A1 | 11/2014 | Hansson et al. | |
| 2014/0350508 A1 | 11/2014 | Popp et al. | |
| 2014/0375297 A1 | 12/2014 | Geiger et al. | |
| 2015/0088086 A1 | 3/2015 | Beck | |
| 2015/0282997 A1 | 10/2015 | Arizti et al. | |
| 2017/0246044 A1 | 8/2017 | Ludwig et al. | |
| 2017/0246052 A1 | 8/2017 | Ludwig et al. | |
| 2017/0246053 A1 | 8/2017 | Ludwig et al. | |
| 2017/0252233 A1 | 9/2017 | Barnhorst et al. | |

(56) References Cited

U.S. PATENT DOCUMENTS

| | | | |
|---|---|---|---|
| 2018/0344544 A1 | 12/2018 | Tally et al. | |
| 2018/0369029 A1 | 12/2018 | Barnhorst et al. | |
| 2019/0060130 A1 | 2/2019 | Tally et al. | |
| 2019/0105206 A1 | 4/2019 | Ludwig et al. | |
| 2019/0374397 A1 | 12/2019 | Tally et al. | |

FOREIGN PATENT DOCUMENTS

| | | |
|---|---|---|
| CN | 202191413 | 4/2012 |
| CN | 202207245 | 5/2012 |
| CN | 202288655 | 7/2012 |
| CN | 202515884 | 11/2012 |
| CN | 202801952 | 3/2013 |
| CN | 204709180 | 10/2015 |
| CN | 204932009 | 1/2016 |
| CN | 106726167 | 5/2017 |
| CN | 206342616 | 7/2017 |
| DE | 3810473 | 10/1989 |
| DE | 102011007818 | 10/2012 |
| DE | 102011007821 | 10/2012 |
| GB | 2080093 | 2/1982 |
| JP | 2003175066 | 6/2003 |
| JP | 2004195083 | 7/2004 |
| JP | 2005304605 | 11/2005 |
| JP | 2009082484 | 4/2009 |
| JP | 2011072657 | 4/2011 |
| JP | 2011072659 | 4/2011 |
| JP | 2011098032 | 5/2011 |
| JP | 2011136063 | 7/2011 |
| JP | 2013255841 | 12/2013 |
| JP | 5690966 | 3/2015 |
| JP | 2016030200 | 3/2016 |
| JP | 2016030201 | 3/2016 |
| JP | 2016030202 | 3/2016 |
| JP | 5934815 | 6/2016 |
| JP | 3205471 | 7/2016 |
| TW | 201626969 | 8/2016 |
| WO | WO-0101907 | 1/2001 |
| WO | WO-03082167 | 10/2003 |
| WO | WO-2010020990 | 2/2010 |
| WO | WO2012143227 | 10/2012 |
| WO | WO 2012143228 | 10/2012 |
| WO | WO2012143230 | 10/2012 |
| WO | WO2012145964 | 11/2012 |
| WO | WO2015046632 | 4/2015 |
| WO | WO 201613258 | 1/2016 |
| WO | WO 201613662 | 1/2016 |
| WO | WO 201613663 | 1/2016 |
| WO | WO 2016104148 | 6/2016 |
| WO | WO2016121183 | 8/2016 |
| WO | WO2016121236 | 8/2016 |
| WO | WO2018199974 A1 | 11/2018 |

OTHER PUBLICATIONS

U.S. Appl. No. 16/106,696, filed Aug. 21, 2018, Tally et al.
All Office Actions for U.S. Appl. No. 16/214,255.
All Office Actions for U.S. Appl. No. 16/106,696.
International Search Report and Written Opinion, PCT/US2017/019010, dated Apr. 11, 2017.
Website: http://www.small-beginnings.com/#!blank/copk, Phototherapy Diapers 'Beary Small' Bili-Buns, 2015.
All Office Actions for U.S. Appl. No. 15/234,235 filed Aug. 11, 2016.
All Office Actions for U.S. Appl. No. 15/440,009, filed Feb. 23, 2017.
All Office Actions for U.S. Appl. No. 15/234,540, filed Aug. 11, 2016.

* cited by examiner

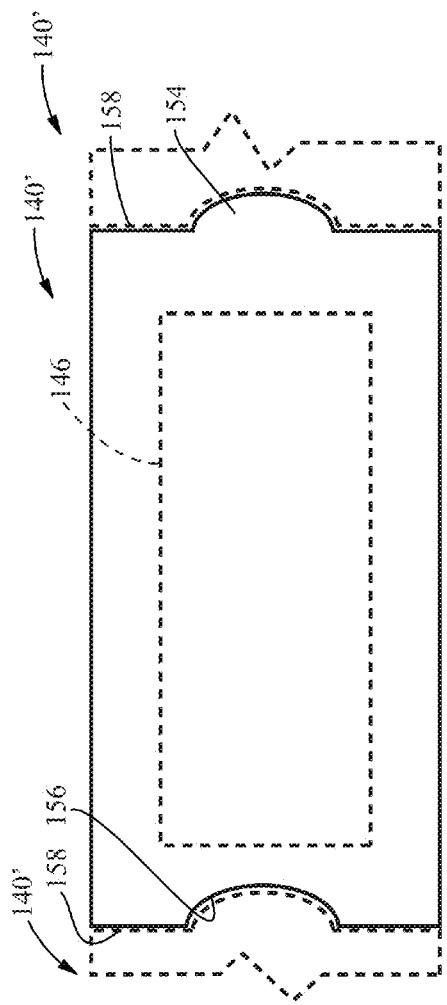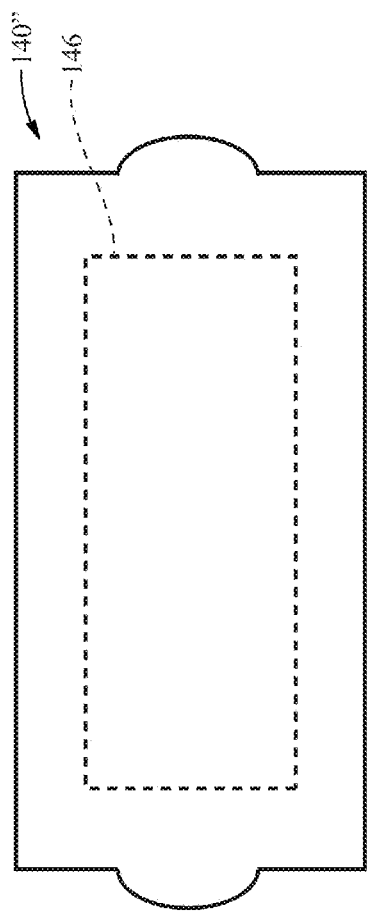

CONFIGURABLE ABSORBENT ARTICLES

CROSS REFERENCE TO RELATED APPLICATIONS

This application claims the benefit, under 35 U.S.C. § 119(e), to U.S. Provisional Patent Application Ser. No. 62/351,325, filed on Jun. 17, 2016 and to U.S. Provisional Patent Application Ser. No. 62/299,794, filed on Feb. 25, 2016, the entire disclosures of which are hereby fully incorporated by reference herein.

FIELD

The present disclosure is directed to configurable absorbent articles.

BACKGROUND

Absorbent articles are used to contain bodily exudates (e.g., urine and BM) in infants, children, and adults. Absorbent articles may be used in hospitals for diapering infants, premature babies, and/or Neonatal Abstinence Syndrome ("NAS") babies. Premature babies, NAS babies, or other small infants may require special care by nurses and other hospital staff. These babies are oftentimes on ventilators, feeding tubes, or other life support or monitoring systems. In some instances, the babies may be positioned within incubators, also known as isolets. The babies are typically kept in high humidity, sterile environments as they have very delicate skin that needs to be protected. It is important to the health of these premature babies that they not be handled too much and that they are maintained in a very sterile environment. Handling the babies too much may cause them stress. Current absorbent articles for premature or NAS babies are somewhat difficult to use and too large for very premature babies, especially in the crotch region. When the current absorbent articles are folded about their lateral axis, they typically take on a rectangular or substantially rectangular shape, thereby providing a wide crotch region. Additionally, current absorbent articles for premature and NAS babies do not provide superior containment of bodily exudates and skin protection from the bodily exudates. Further, the current absorbent articles do not provide all of the features that premature or NAS baby caregivers may view as beneficial. As such, absorbent articles for premature babies, NAS babies, other babies, and other wearers need to be improved.

SUMMARY

The present disclosure provides configurable absorbent articles suitable for premature and NAS babies (and other small infants, other babies, or other wearers), while not being limited to any certain sizes or uses. As discussed above, one issue with current absorbent articles is that they are not configured for the specific needs of premature or NAS babies, in some instances, forcing nurses to handle these babies more than the nurses' desire. The configurable absorbent articles of the present disclosure overcome the disadvantages of current premature and/or NAS baby absorbent articles by providing very narrow crotch regions, narrow chassis regions, small overall dimensions, soft skin-contacting surfaces, front and back umbilical cord notches (in some forms to create a reversible absorbent article), front and back reverse umbilical cord projections (in some forms to create a reversible absorbent article), discrete and detachable fastening members (to allow nurses to configure the absorbent articles as needed and have fastening flexibility), one or more wetness guards, and/or low opacity outer cover nonwovens and/or backsheets, for example. The discrete and detachable fastening members may have slots or apertures formed therein, so that tubes or hoses used to aid or monitor the health of the premature or NAS babies may be inserted therethrough without disturbing the baby or without the need for moving the baby. These slots or apertures may also help hold the tubes or hoses in place. Low opacity backsheets and/or outer cover nonwoven materials may be helpful in identifying when the absorbent article needs changed without the need for moving the babies. In some forms, the configurable absorbent articles of the present disclosure may allow for use without any fastening members, owing to the discrete and detachable fastening members. This may be desired by nurses in some instances and may reduce the need to touch or move the baby. Furthermore, the absorbent articles of the present disclosure may also be reversible to allow the nurse to apply the absorbent article as he/she desires or as is needed. Absorbent materials in absorbent cores of the absorbent articles may be homogeneous to allow for reversible use. Further, the absorbent cores may have an extended hourglass shape to help narrow the crotch region and provide for more fit options and leg placements.

The absorbent articles of the present disclosure may comprise one or more wetness guards. The wetness guards may comprise one or more liquid impermeable materials, such as films or nonwoven materials, and one or more non-film materials, such as one or more nonwoven materials. The wetness guards may be positioned in areas of the absorbent articles that come into contact with a baby's lower back, waist, and/or legs, but not be positioned where a crotch area of the baby contacts the absorbent article. The non-film material may face toward the baby to provide comfort, while the liquid impermeable material may face away from the baby. The wetness guards may accomplish at least two functions. First, when a baby urinates, the urine is typically wicked away from the point of entry into the absorbent core throughout the absorbent core (both laterally and longitudinally). This may cause areas of the absorbent pad where the baby's lower back, waist, and/or legs are to be wet. The wetness guards provide a barrier between the wet areas and the baby's lower back, waist, and/or legs thereby leading to improved skin health for the baby. Second, the wetness guards may comprise soft non-film materials facing the baby's skin. As such, the baby's lower back, waist, and/or legs may rest on a soft, comfortable material again leading to improved skin health.

These and other advantages of the configurable absorbent articles of the present disclosure are set forth herein in greater detail.

The present disclosure is directed, in part, to an absorbent article comprising a central lateral axis, a central longitudinal axis, a first end edge, a second end edge opposing the first end edge, a first side edge, a second side edge opposing the first side edge, a first waist region on a first side of the central lateral axis, a second waist region on a second side of the central lateral axis, and a crotch region extending intermediate the first waist region and the second waist region and crossing the central lateral axis. The absorbent article comprises a liquid permeable, apertured or nonapertured topsheet. The topsheet may be hydrophobic or hydrophilic, or may have hydrophilic or hydrophobic portions or layers. The absorbent article comprises a liquid impermeable backsheet, an acquisition material, and an absorbent core positioned at least partially intermediate the acquisition material and the liquid impermeable backsheet. The absorbent core comprises an absorbent material. The absorbent material may have a first width, in a direction parallel to the central lateral axis, in the first waist region. The absorbent material may have a second width, in the direction parallel to the lateral axis, in the second waist region. The absorbent material may have a third width, in the direction parallel to the lateral axis, in the crotch region. The first width and the second width may be greater than the third width and the first and second widths may be the same, substantially the same, or different. The absorbent article comprises a pair of leg cuffs positioned proximal to the first and second side edges. The absorbent article comprises a first wetness guard in the first waist region. The first wetness guard may comprise a first liquid impermeable material in a facing relationship with the topsheet and a second liquid permeable material forming a first portion of a wearer-facing surface of the absorbent article. The absorbent article may comprise a second wetness guard in the second waist region. The second wetness guard may comprise a third liquid impermeable material in a facing relationship with the topsheet and a fourth liquid permeable material forming a second portion of the wearer-facing surface of the absorbent article. The absorbent article may comprise a removable fastening member comprising a first surface, a second surface opposite to the first surface, a first end, a second end opposite to the first end, a first fastener comprising a first plurality of hooks on the first surface and positioned proximate to the first end, and a second fastener comprising a second plurality of hooks on the first surface and positioned proximate to the second end.

The present disclosure is directed, in part, to an absorbent article comprising a central lateral axis, a central longitudinal axis, a first end edge, a second end edge opposing the first end edge, a first side edge, a second side edge opposing the first side edge, a first waist region on a first side of the central lateral axis, a second waist region on a second side of the central lateral axis, and a crotch region extending intermediate the first waist region and the second waist region and crossing the central lateral axis. The absorbent article comprises a liquid permeable topsheet, a liquid impermeable backsheet, and an absorbent core positioned at least partially intermediate the topsheet and the liquid impermeable backsheet. The absorbent core comprises an absorbent material. The absorbent material may have a first width, in a direction parallel to the central lateral axis, in the first waist region. The absorbent material may have a second width, in the direction parallel to the lateral axis, in the second waist region. The absorbent material may have a third width, in the direction parallel to the lateral axis, in the crotch region. The first width and the second width may be greater than the third width. The first and second widths may the same, substantially the same, or different. The absorbent article comprises a pair of leg cuffs positioned proximal to the first and second side edges and a first wetness guard in the first waist region. The first wetness guard may comprise a first liquid impermeable material in a facing relationship with the topsheet and a second liquid permeable material forming a first portion of a wearer-facing surface of the absorbent article. The absorbent article may comprise a second wetness guard in the second waist region. The second wetness guard may comprise a third liquid impermeable material in a facing relationship with the topsheet and a fourth liquid permeable material forming a second portion of the wearer-facing surface of the absorbent article. The absorbent article may comprise a removable fastening member comprising a first surface, a second surface opposite to the first surface, a first end, a second end opposite to the first end, a first fastener comprising a first plurality of hooks on the first surface and positioned proximate to the first end, and a second fastener comprising a second plurality of hooks on the first surface and positioned proximate to the second end.

The present disclosure is directed, in part, to an absorbent article comprising a central lateral axis, a central longitudinal axis, a first end edge, a second end edge opposing the first end edge, a first side edge, a second side edge opposing the first side edge, a first waist region on a first side of the central lateral axis, a second waist region on a second side of the central lateral axis, and a crotch region extending intermediate the first waist region and the second waist region and crossing the central lateral axis. The absorbent article may comprise a liquid permeable, apertured or non-apertured topsheet. The topsheet may be hydrophilic or hydrophobic, or may have hydrophobic or hydrophilic portions or layers. The absorbent article may comprise a liquid impermeable backsheet, an acquisition material, and an absorbent core positioned at least partially intermediate the acquisition material and the liquid impermeable backsheet. The absorbent core comprises an absorbent material. The absorbent material may have a first width, in a direction parallel to the central lateral axis, in the first waist region. The absorbent material may have a second width, in the direction parallel to the lateral axis, in the second waist region. The absorbent material may have a third width, in the direction parallel to the lateral axis, in the crotch region. The first width and the second width may be greater than the third width. The first width and the second width may be the same, substantially the same, or different. The absorbent article comprises a pair of leg cuffs positioned proximal to the first and second side edges, respectively, and a first wetness guard in the first waist region. The first wetness guard may comprise a first liquid impermeable material in a facing relationship with the topsheet and a second liquid permeable material forming a first portion of a wearer-facing surface of the absorbent article. The absorbent article may comprise a second wetness guard in the second waist region. The second wetness guard may comprise a third liquid impermeable material in a facing relationship with the topsheet and a fourth liquid permeable material forming a second portion of the wearer-facing surface of the absorbent article. The first wetness guard overlaps a first portion of the absorbent core and the second wetness guard overlaps a second, different portion of the absorbent core. The first wetness guard may be a discrete component that is joined to a first portion of the topsheet and/or first portions of the leg cuffs. The second wetness guard may be a discrete component that is joined to a second portion of the topsheet and/or second portions of the leg cuffs. The absorbent article may comprise a removable fastening member comprising a first surface, a second surface opposite to the first surface, a first end, a second end opposite to the first end, a first fastener comprising a first plurality of hooks on the first surface and positioned proximate to the first end, and a second fastener comprising a second plurality of hooks on the first surface and positioned proximate to the second end. The absorbent article comprises an outer cover material joined to a non-absorbent core facing side of the backsheet. The outer cover material or the backsheet may comprise a first graphic in the first waist region. The outer cover material or the backsheet may comprise a second graphic in the second waist region. The second graphic may be a mirror image of the first graphic relative to the central longitudinal axis to indicate reversibility of the absorbent article to a caregiver.

The various absorbent articles may be placed in packages. The packages may be sold in arrays or on-line arrays.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

FIG. 33 is a plan view of another example insert for use with an absorbent article;

FIG. 34 is a plan view of another example insert for use with an absorbent article;

DETAILED DESCRIPTION

Various non-limiting forms of the present disclosure will now be described to provide an overall understanding of the principles of the structure, function, manufacture, and use of the configurable absorbent articles disclosed herein. One or more examples of these non-limiting forms are illustrated in the accompanying drawings. Those of ordinary skill in the art will understand that the configurable absorbent articles specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the terms "join" and "joined" encompass configurations whereby an element is directly secured to another element by affixing the element directly to the other element, and configurations whereby an element is indirectly secured to another element by affixing the element to intermediate member(s) which in turn are affixed to the other element.

As used herein, the term "array" means a display of packages comprising disposable absorbent articles of different sizes having like article constructions. Packages for the absorbent articles have the same brand and/or sub-brand, and the packages are oriented in proximity to each other in a given area of a retail store. An array is marketed as a line-up of products normally having like packaging elements (e.g., packaging material type, film, paper, dominant color, design theme, etc.) that conveys to consumers that the different individual packages are part of a larger line-up. Arrays often have the same brand, for example, "Pampers®." In other instances, the arrays may have brands from the same manufacturer, such as "Pampers®" and "Luvs®", for example.

Arrays also often have the same trademarks, including trademarks of the brand, sub-brand, and/or features and/or benefits across a line-up.

As used herein, the term "on-line array" means an "array" distributed by a common on-line source.

Figure 1:
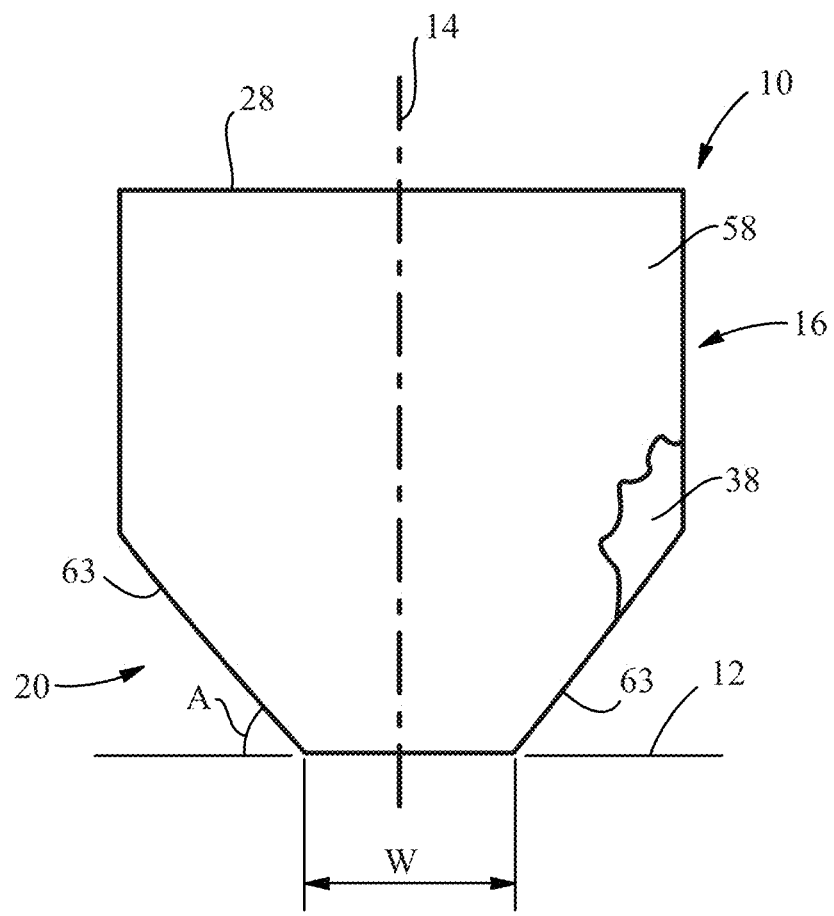
FIG. 1 is a plan view of an example absorbent of the present disclosure.
Figure 2:
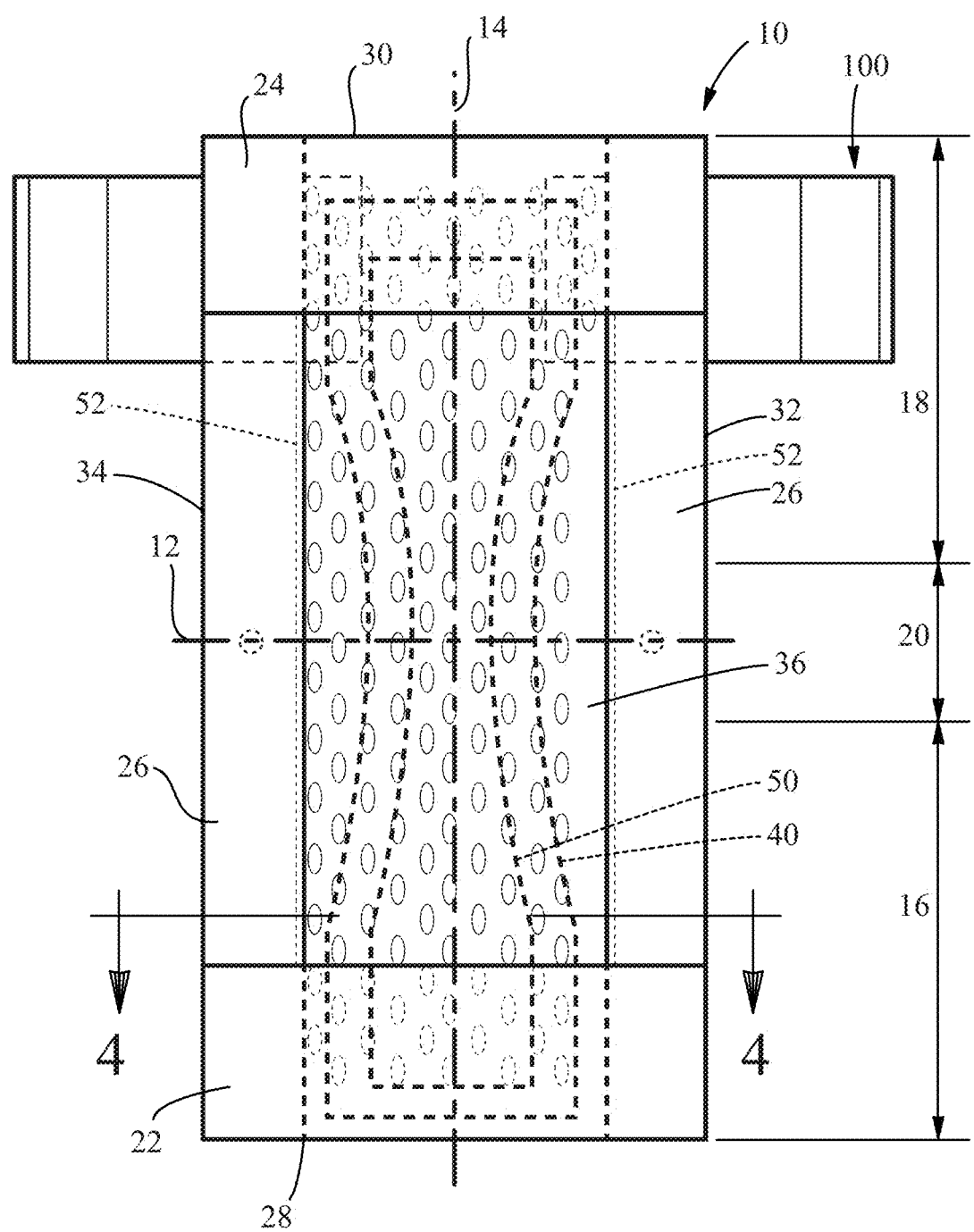
FIG. 2 is a plan view of an example absorbent article of the present disclosure, wearer-facing surface facing the viewer.
Figure 3:
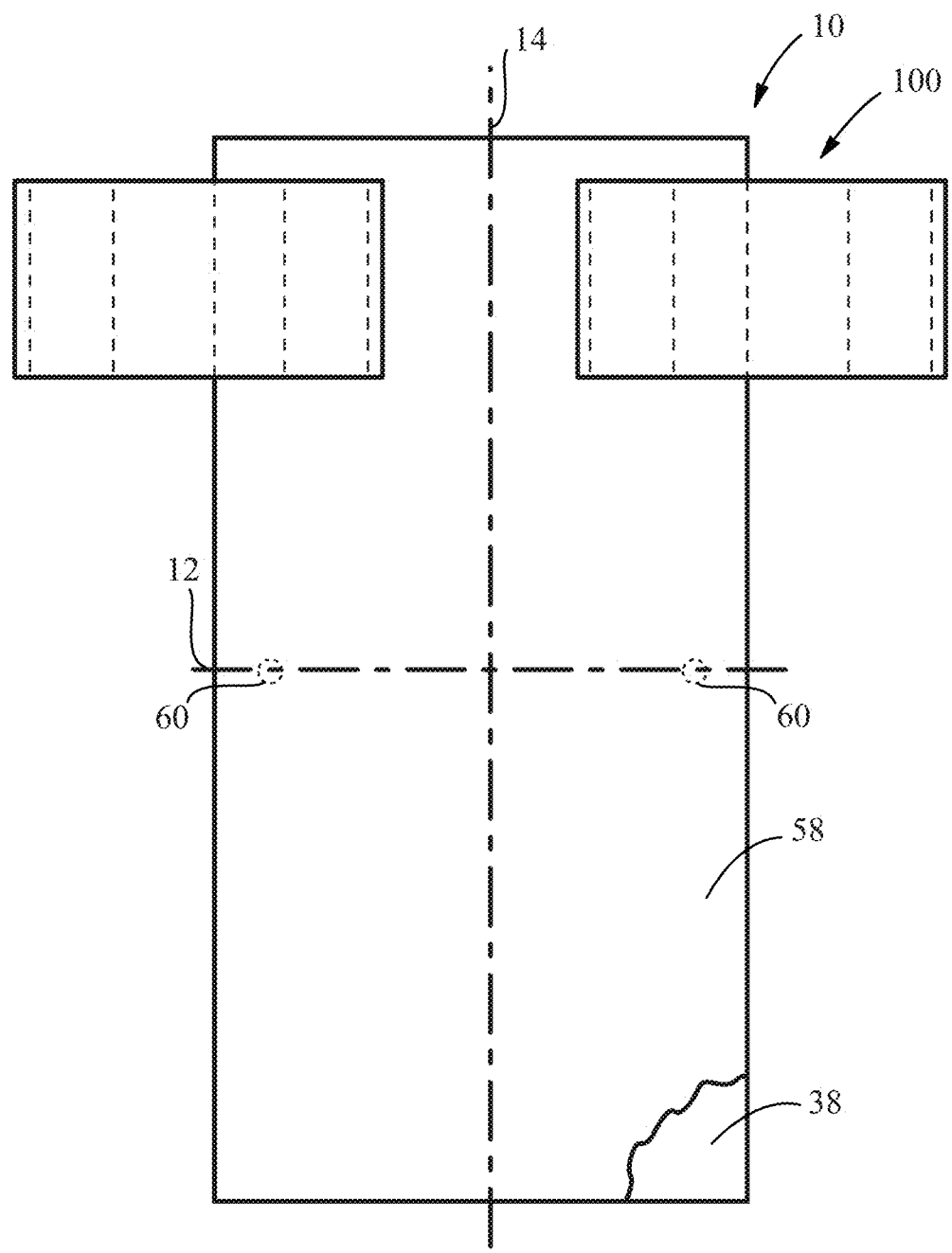
FIG. 3 is a plan view of the absorbent article of FIG. 2, garment-facing surface facing the viewer.
Figure 4:
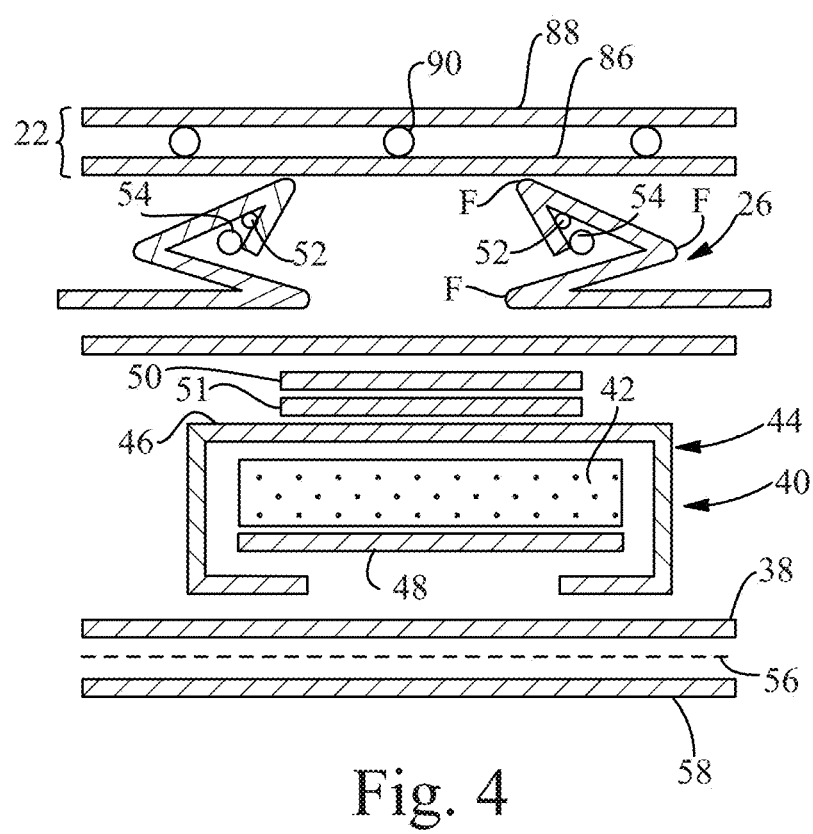
FIG. 4 is a cross-sectional view of the absorbent article of FIG. 2, taken about line 4-4.

Configurable absorbent articles that provide improved fit, more flexible application options, narrow crotch regions, bodily exudate containment and improved skin health for premature, NAS, and other babies (or other wearers) are provided herein. FIG. 1 is a plan view of an absorbent article 10 folded about its lateral axis, garment-facing surface of a first waist region or a front waist region facing the viewer. FIG. 2 is a plan view of the absorbent article 10 of FIG. 1, with the absorbent article 10 laid flat with the elastics extended, wearer-facing surface facing the viewer. FIG. 3 is a plan view of the absorbent article 10 of FIG. 2, with the absorbent article 10 laid flat with the elastics extended, garment-facing surface facing the viewer. FIG. 4 is a cross-sectional view of the absorbent article 10 of FIG. 2, taken about line 4-4. The absorbent article 10 may comprise a lateral axis 12, a longitudinal axis 14, a first waist region or a front waist region 16, a second waist region or a back waist region 18, and a crotch region 20. In a reversible absorbent article, the "first" and "second" waist regions 16 and 18 may be referred to in the claims since the absorbent article can be applied in either direction. The absorbent article 10 may have a first wetness guard 22 and a second wetness guard 24. In some instances, only one wetness guard may be provided on the absorbent articles of the present disclosure. The single wetness guard may be provided on either side of the lateral axis 12 of the absorbent articles 10. The absorbent articles 10 may also comprise cuffs 26 or raised barriers for containing bodily exudates so that they may be absorbed by an absorbent core.

The absorbent articles 10 may comprise a first end edge 28 on a first side of the lateral axis 12 and a second end edge 30 on a second side of the lateral axis 12. The absorbent articles 10 may comprise a first side edge 32 on a first side of the central longitudinal axis 14 and a second side edge 34 on a second side of the central longitudinal axis 14. The absorbent articles 10 may comprise a liquid permeable material or liquid permeable topsheet 36, a liquid impermeable material or liquid impermeable backsheet 38, and an absorbent core 40 positioned at least partially intermediate the topsheet 36 and the backsheet 38.

The topsheet 36, the backsheet 38, and the absorbent core 40 may be manufactured of any suitable materials. Suitable topsheet materials may comprise porous foams, reticulated foams, apertured plastic films, or woven or nonwoven webs of natural fibers (e.g., wood or cotton fibers), synthetic fibers (e.g., polyester or polypropylene fibers), non-apertured material, apertured materials, apertured nonwoven materials, apertured nonwoven materials that are produced using an overbonding and ring rolling process, or a material having a combination of natural and synthetic fibers. Spunbond high loft materials may also be used, whether apertured or non-apertured. The topsheet 36 may have an embossed pattern, graphics, patterned, indicia, and/or three-dimensional features, either along with or instead of apertures. In some instances, the topsheet 36 may be a planar topsheet. In other instances, the topsheet may be a topsheet like that disclosed in U.S. Patent Application Publication No. 2015/0250662, to Isele et al., filed on Mar. 2, 2015 or in U.S. Patent Application Publication No. 2016/0136014, to Arora et al., filed on Nov. 5, 2015. The topsheet may be hydrophobic or hydrophilic. If the topsheet is apertured, it may be desirably to have the topsheet by hydrophobic.

Suitable backsheet materials may comprise breathable materials or highly breathable materials that permit vapors to escape from the absorbent article 10 while still preventing, or at least inhibiting, bodily exudates from passing through the backsheet 34 (i.e., liquid impermeable materials). Such materials may comprise nonwoven materials, woven materials, films, and/or laminates comprising a combination of one or more of these materials. Other backsheet materials may be non-breathable materials, such as films, for example.

One measure of the breathability of a backsheet or backsheet/outer cover nonwoven material laminate is the perviousness of the backsheet or the laminate to the passage of water vapor, reflected by the moisture vapor transmission rate (MVTR) of the backsheet or laminate. The MVTR of the laminate or backsheet may be in the range of about 500 $g/m^2/24$ hr to about 5000 $g/m^2/24$ hr, about 1000 $g/m^2/24$ hr to about 4000 $g/m^2/24$ hr, or about 2000 $g/m^2/24$ hr to about 3000 $g/m^2/24$ hr, specifically reciting all 0.1 $g/m^2/24$ hr increments within the above-referenced ranges and all ranges formed therein or thereby.

The MVTR can be determined by placing a quantity of a hydrophilic material, such as calcium chloride, into a non-porous, open-top vessel (not shown) having an outwardly-extending flange around the vessel opening. A portion of the material for which the MVTR is to be determined is placed in overlying relationship relative to the vessel opening and is in contact with the flange of the vessel to completely cover the open end of the vessel. An annular gasket and an annular retaining ring are then placed over the material to be tested and are securely clamped to the vessel flange by any convenient clamping arrangement, to tightly and completely seal the periphery of the vessel opening in order that transmission of air or moisture vapor can only occur through the material being tested. The resulting assembly is then weighed to determine the initial weight of the vessel and its contents.

After the initial weight has been determined, the assembly is placed in a chamber having a constant temperature (40° C.) and a constant humidity (75% relative humidity). The vessel is maintained under those atmospheric conditions for a period of five (5) hours, after which it is removed from the chamber, wrapped tightly with an impervious film to prevent transfer of moisture into and out of the vessel, and is allowed to reach thermal equilibrium with the ambient atmosphere in which the weigh balance is located. Thermal equilibrium is achieved in about 30 minutes, after which the film overwrap is removed from the vessel, which is again weighed to determine the final weight of the vessel and its contents.

The MVTR is calculated by the following formula, which provides the MVTR in g/m²/24 hr:

$$MVTR = \frac{(\text{Final Wt(gm)} - \text{Initial Wt(gm)}) \times 24.0}{\text{Sample Area (sq. meters)} \times 5.0 \text{ hr.}}$$

Figure 5:
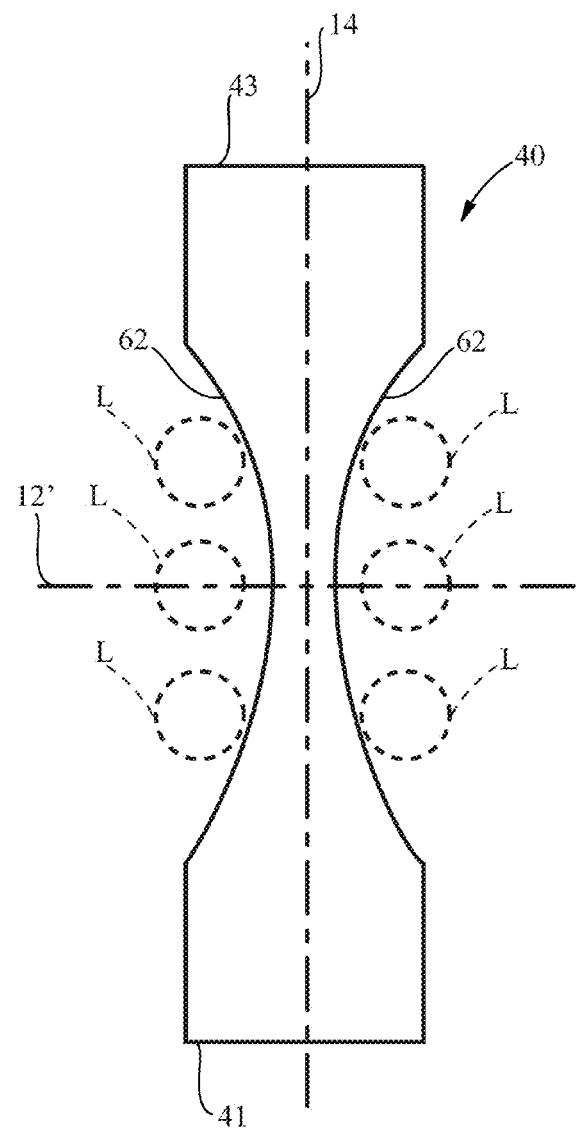
FIG. 5 is a plan view of an example absorbent core for the absorbent articles of the present disclosure having an extended hourglass shape.

A suitable absorbent core 40 for use in the absorbent articles 10 of the present disclosure may comprise any absorbent material 42 which is generally compressible, conformable, non-irritating to the wearer's skin, and capable of absorbing and retaining bodily exudates. In addition, the configuration and construction of the absorbent core 40 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In other instances, the configuration and construction of the absorbent core 40 may be uniform and homogeneous, such that the absorbent article 10 can be reversible. In such an instance, the absorbent material 42 may be uniform and homogeneous (i.e., not profiled). In some forms, the absorbent core 40 may have an hourglass shape, an extended hourglass shape, or rectangular shape, for example. FIG. 5 is a plan view of an example absorbent core 40 having an extended (extended about the longitudinal axis 14) hourglass shape. In an instance, the absorbent material 42 may have an hourglass shape and the absorbent core 40 may be rectangular (i.e., the core bag is rectangular and the absorbent material 42 has an hourglass shape). The absorbent material 42 and/or the absorbent core 40 as a whole (including the core bag) may have a first width, in a direction parallel to the lateral axis 12, in the first waist region 16, may have a second width, in the direction parallel to the lateral axis 12, in the second waist region 18, and may have a third width, in the direction parallel to the lateral axis 12, in the crotch region 20. The first and second widths may be greater than the third width. The first and second widths may be the same, substantially the same, or different. In some instances, the absorbent material 42 may have the shape illustrated in FIG. 5 that is then surrounded by a rectangular core bag.

The absorbent material 42 may comprise superabsorbent polymers, co-form, foams (including but not limited to High Internal Phase Emulsion foams), air-felt (cellulosic material), or mixtures thereof. In some forms the absorbent material 42 may comprise less than 30%, less than 35%, less than 40%, at least 40%, at least 50%, at least 75%, at least 80%, at least 85%, at least 90%, at least 95%, at least 97%, at least 98%, at least 99%, or 100% superabsorbent polymers, by weight of the absorbent material. In other forms, the absorbent material 42 may only comprise air-felt and may be free of, or substantially free of (e.g., less than 5% by weight of the absorbent material) any superabsorbent polymers. The absorbent material 42 may have air-felt and less than 15% of superabsorbent polymers, less than 10% of superabsorbent polymers, less than 5% of superabsorbent polymers, less than 3% of superabsorbent polymers, or less than 1% of superabsorbent polymers. In other forms, the absorbent material 42 may comprise a mixture of air-felt and superabsorbent polymers (e.g., 30% to 70% air-felt and 30% to 70% superabsorbent polymers).

Referring to FIG. 4, the absorbent material 42 may be enclosed in a core bag 44. The core bag 44 may comprise a first substrate 46 at least partially on a first side of the absorbent material 42 and a second substrate 48 at least partially on a second side of the absorbent material 42. The first substrate 46 may form a C-wrap around portions of the absorbent material 42 and the second material 48 to enclose the absorbent material 42. In other instances, the core wrap may have any suitable configuration known to those of skill in the art. In some forms, the absorbent core 40 may comprise one or more absorbent material free areas or channels, or substantially absorbent material free areas (e.g., areas with substantially no superabsorbent polymers or air-felt). In this instance, the first substrate 46 may be joined, bonded, or glued to the second substrate 48 in these areas or channels. In other forms, channels may be embossed into the absorbent core 40. Some example channel and absorbent core configurations are described in further detail in U.S. Pat. Nos. 8,979,815, 9,216,118, and 9,216,116.

Referring to FIGS. 2 and 4, the absorbent articles 10 may comprise one or more acquisition materials 50. The absorbent articles 10 may also comprise one or more optional distribution materials 51 (FIG. 4) either between the topsheet 32 and the acquisition material 50 or between the acquisition material 50 and core bag 44. In some instance, the acquisition material 50 and/or the distribution material 51 may extend the full width and/or length of the core bag 44. In other instances, the acquisition material 50 and/or distribution material 51 may extend less than the full width and/or length of the core bag 44. The acquisition material 50 or the distribution material 51 may have a rectangular shape, an hourglass shape, or an extended hourglass shape, for example. The acquisition material 50 may be used to aid the topsheet 36 in acquiring bodily exudates and moving the bodily exudates into the absorbent core 40. The distribution material 51, if provided, may help the absorbent articles 10 distribute bodily exudates above the absorbent core 40. As an example, the acquisition material may be a nonwoven material and the distribution material may be cross-linked cellulosic fibers, tissue, or another nonwoven material, for example. In some instances, only an acquisition material may be provided, only a distribution may be provided, or neither may be provided depending on the desired properties of a particular absorbent article.

Figure 6:
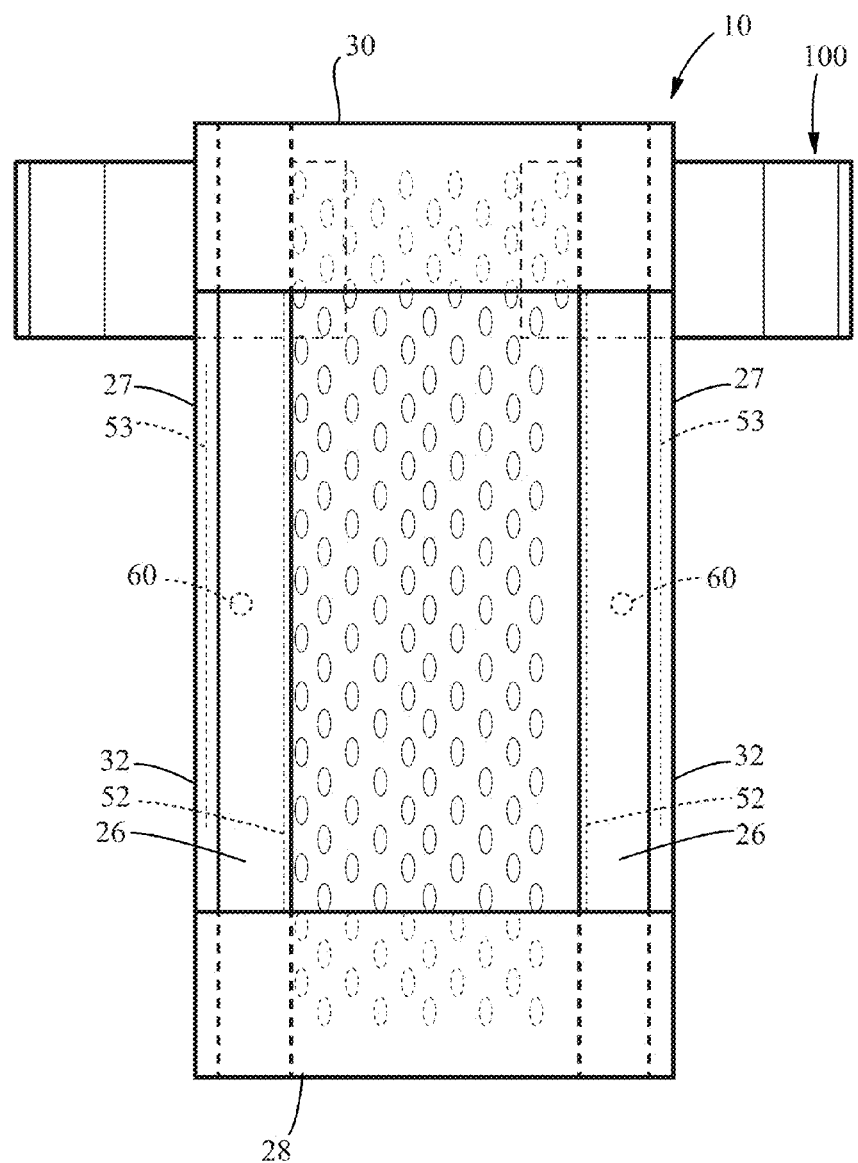
FIG. 6 is a plan view of another absorbent article of the present disclosure, wearer-facing surface facing the viewer.

Referring to FIGS. 2 and 4, the pair of cuffs 26 may extend at least partially between, or fully between, the first end edge 28 and the second end edge 30. The cuffs 26 may or may not have one or more elastics 52. In some instances, if the cuffs 26 do not have elastics 52 they may be pre-strained prior to being joined to the absorbent articles 10 so that they may still stand (i.e., extend upwardly) relative to the topsheet 36. In other instances, the cuffs 26 that are free of elastics may not be pre-strained. In some instances, only a single pair of cuffs may be provided to aid in helping narrow the crotch region 20. In some forms, referring to FIG. 6, a second pair of cuffs 27 may be provided in addition to the first pair of cuffs 26. In an instance, the second pair of cuffs 27 may be free of elastics and may or may not be pre-strained. In other instances, each of the cuffs 26 or 27 may have one or more elastics 52 and 53, respectively. The elastics 52 and/or 53 may cause the cuffs to stand (i.e., extend upwardly) relative to the topsheet 36. The elastics 52 and 53 may have any suitable length along the longitudinal axis 14. In a form, the cuffs 26 (or 27) may each have three longitudinally extending folds (labeled F in FIG. 4) to allow them to stand and extend a suitable distance from the topsheet 36. Glue or bonding of the cuffs is indicated at 54 in FIG. 4. In other forms, the cuffs 26 or 27 may have any suitable configuration. The cuffs generally aid bodily exudate containment to the area of the absorbent core 40 and reduce side edge leakage. Contracted and/or standing portions of the cuffs 26 and/or 27 may be more prominent on a first side of the lateral axis 12 or the second side of the lateral axis 14. In other instances, the contracted and/or standing portions of the cuffs 26 and/or 27 may be the same on both sides of the central lateral axis 12. In some instances, the cuffs 26 and/or 27 may extend the same distance on each side of the central lateral axis 12. In some instances, the absorbent articles 10 may not comprise any cuffs.

In other instances, the absorbent articles 10 may not comprise any cuffs, but some form of raised barriers may be used in their place. A pair of raised barriers may be attached to the topsheet 36, positioned under the topsheet 36, or formed from a portion of the topsheet 36 and/or acquisition or distribution materials. The raised barriers may comprise flexible foams, liquid impermeable materials, nonwoven materials, films, and/or other suitable materials. The raised barriers may be "raised" relative to the topsheet 36 and may act in a similar fashion as the cuffs 26 and 27, thereby causing bodily exudates to remain over the absorbent core 40 such that they can be absorbed by the absorbent core 40. The raised barriers may have any suitable thickness measured in a direction parallel to the lateral axis 12, such as 2 mm to 10 mm, for example. In some instances, one raised barrier may be provided and this single raised barrier may fully surround, or partially surround, the absorbent core 40 or portions thereof. The raised barriers may be raised a suitable amount from the topsheet 36 to contain the bodily exudates within the absorbent articles 10, such as in the range of 1 mm to 30 mm, or 2 mm to 20 mm, for example. Further details regarding raised barriers, including example structures and shape can be found in U.S. Patent Appln. Publ. No. 2014/0171898 to Greening II, et al. The raised barriers may be used with at least one pair of cuffs as well for better containment. The cuffs may be positioned laterally inboard or laterally outboard of the raised barriers. The raised barriers or the cuffs 26, 27 may be referred to as "bodily exudate containment means".

Referring to FIGS. 1, 3, and 4, an outer cover nonwoven material 58 may be positioned on a non-absorbent core-facing side of the backsheet 38. The outer cover nonwoven material 58 may be joined to the backsheet 38 using an adhesive 56, for example. The outer cover nonwoven material 58 may be formed of one or more layers and typically may be a soft material. The outer cover nonwoven material 58 may comprise a plurality of bonds, embossments, or three-dimensional features to provide a more consumer appealing appearance or for other reasons.

Figure 7:
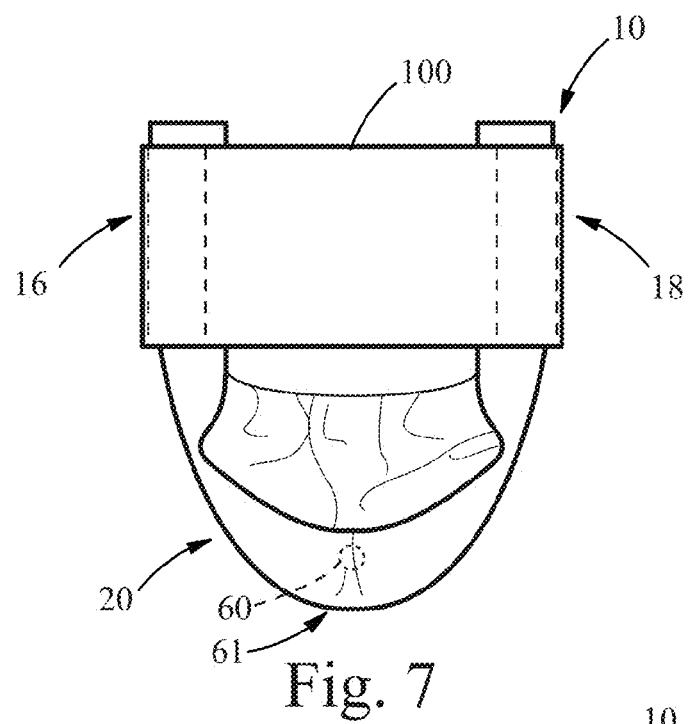
FIG. 7 is a left side view of an example absorbent article comprising a discrete fastening member of the present disclosure.
Figure 8:
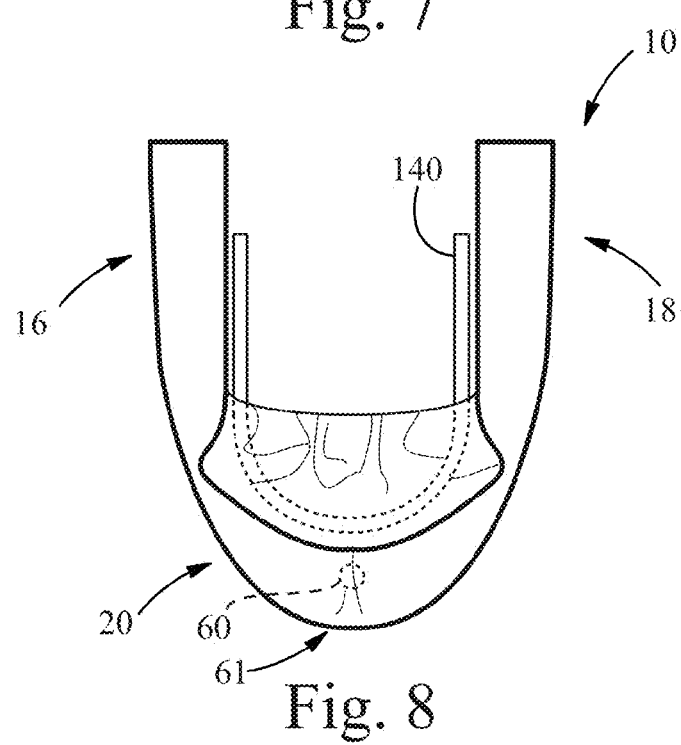
FIG. 8 is another left side view of an example absorbent article of the present disclosure without a discrete fastening member.
Figure 9:
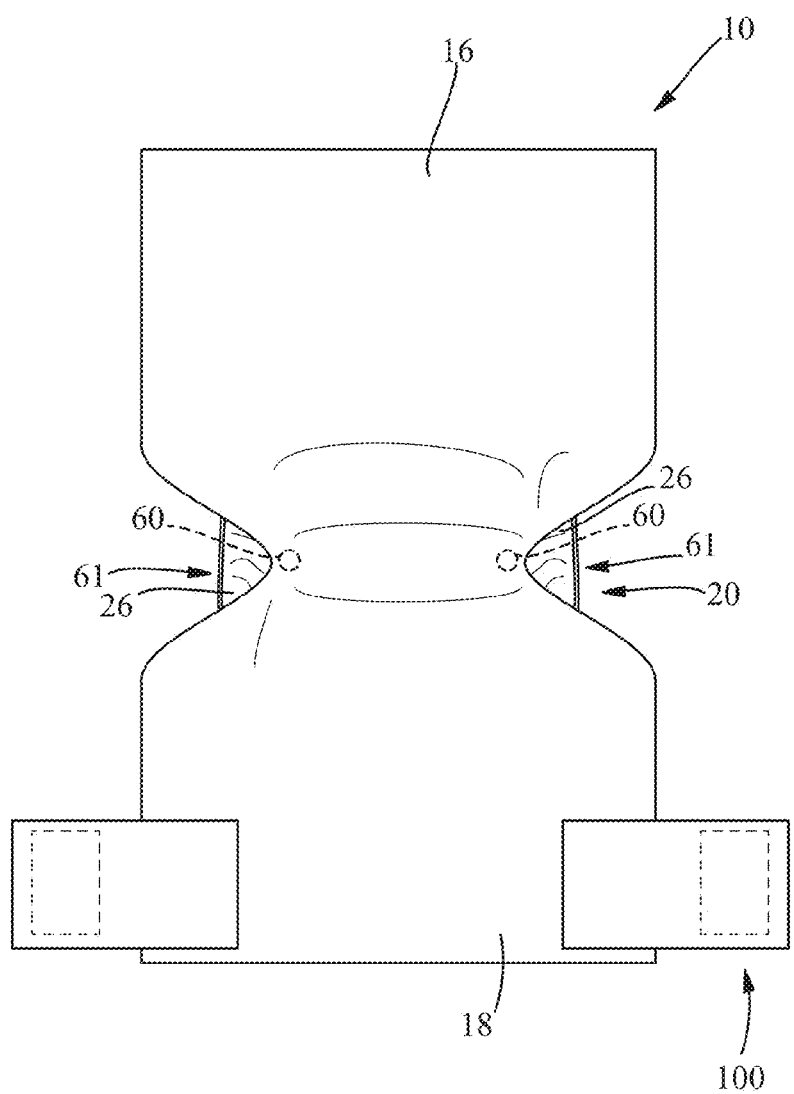
FIG. 9 is a perspective view of an example absorbent article of the present disclosure comprising crotch folds created by crotch narrowing joints.

FIG. 7 is a side view of the absorbent article of FIG. 1 with a fastening member 100. FIG. 8 is a side view of the absorbent article of FIG. 1 without the fastening member 100. FIG. 9 is a perspective view of the absorbent article of FIG. 1, garment-facing surface facing the viewer.

Referring to FIGS. 2, 3, and 6-9, the absorbent articles 10 of the present disclosure may comprise a pair of crotch narrowing joints 60 in the crotch region 20. In other forms, only one side of the crotch region 20 may comprise a crotch narrowing joint 60. The crotch narrowing joints 60 may be created when a wearer-facing portion of the outer cover nonwoven material 58 or a wearer-facing portion of the cuffs 26 or 27 (if a second set of cuffs is provided) is joined to a standing portion or other portion of the cuffs 26 or 27 (if a second set of cuffs is provided) or to a portion of the topsheet 36. The joint may be an adhesive bond, a mechanical bond, a thermal bond, and/or any other suitable type of bond, or joinder. In other instances, the crotch narrowing joints 60 may be formed by joining a wearer-facing portion of the backsheet 38 (or laminate comprising the backsheet 38 and outer cover nonwoven material 58) to a portion of the cuffs 26 or 27 or to a portion of the topsheet 36. In any event, portions of the outer cover nonwoven material 58 proximate to the first and second side edges 32 and 34 may be joined directly or indirectly to a portion of the cuffs 26 or 27 or a portion of the topsheet 36. By providing these crotch narrowing joints 60, the absorbent articles 10 are able to achieve a narrow folded crotch width, ("W" in FIG. 1) at or proximate to the lateral axis 12. This narrow folded crotch width may be especially important for premature babies for a number of reasons. First, smaller babies have less space in between their legs. Thus, the smaller the folded crotch width, the better the absorbent articles will fit them without applying any leg separating forces on their legs, thereby allowing the legs to rest in a comfortable position, such as near the body midline, for example. Second, in a typical diaper, the inner thigh areas of the legs of the baby may be in contact with portions of the cuffs and/or the backsheet. In the absorbent articles 10 of the present disclosure the baby's inner thigh areas may be in contact with portions of the cuffs 26 and/or 27 and portions of the soft outer cover nonwoven material 58, thereby providing a more comfortable wearer experience and at times reducing inner thigh chafing.

Referring to FIGS. 7-9, the crotch narrowing joints 60 cause portions of the crotch region 20 to fold inwardly toward the longitudinal axis 14, when the elastics of the cuffs are at least partially relaxed, thereby creating crotch folds 61. Referring to FIG. 1, these crotch folds 61 provide for the narrow folded crotch width W. The crotch folds 61 also provide the absorbent article 10 with angled portions 63 in the crotch region 20. The angled portions 63 may have an angle in the range of about 10 degrees to about 80 degrees, about 15 degrees to about 75 degrees, about 20 degrees to about 70 degrees, about 30 degrees to about 60 degrees, about 40 degrees to about 60 degrees, relative to the lateral axis 12, specifically reciting all 0.1 degree increments within the specified ranges and all ranges formed therein or thereby. All angles are measured according to the Folded Crotch Angle Test herein.

Referring to FIG. 5, in addition to the crotch narrowing joints 60, the absorbent core 40 may have an extended hourglass shape with leg notches 62 elongated in a direction parallel to the longitudinal axis 14. This feature allows for the legs ("L") to be positioned at multiple locations within the leg notches 62 to fit different wearers and situations. The legs of a wearer, for example, may be positioned more proximate to a first end edge 41 or more proximate to a second end edge 43 of the absorbent core 40 to suit certain situations or positions of the baby. As referenced above, the acquisition materials 50 and/or distribution materials 51 may have a similar shape or a different shape. The absorbent core 40 may have a width measured along its lateral axis 12' in the range of about 5 mm to about 300 mm, about 10 mm to about 100 mm, about 15 mm to about 75 mm, about 15 mm to about 40 mm, about 15 mm to about 25 mm, or about 20 mm, specifically reciting all 0.1 mm increments within the specified range and all ranges formed therein or thereby. The absorbent core 40 may have a width measured along either the first end edge 41 or the second end edge 43 in the range of about 15 mm to about 500 mm, about 20 mm to about 300 mm, about 25 mm to about 100 mm, about 30 mm to about 50 mm, about 35 mm to about 40 mm, or about 38 mm, specifically reciting all 0.1 mm increments within the specified range and all ranges formed therein or thereby.

Figure 10:
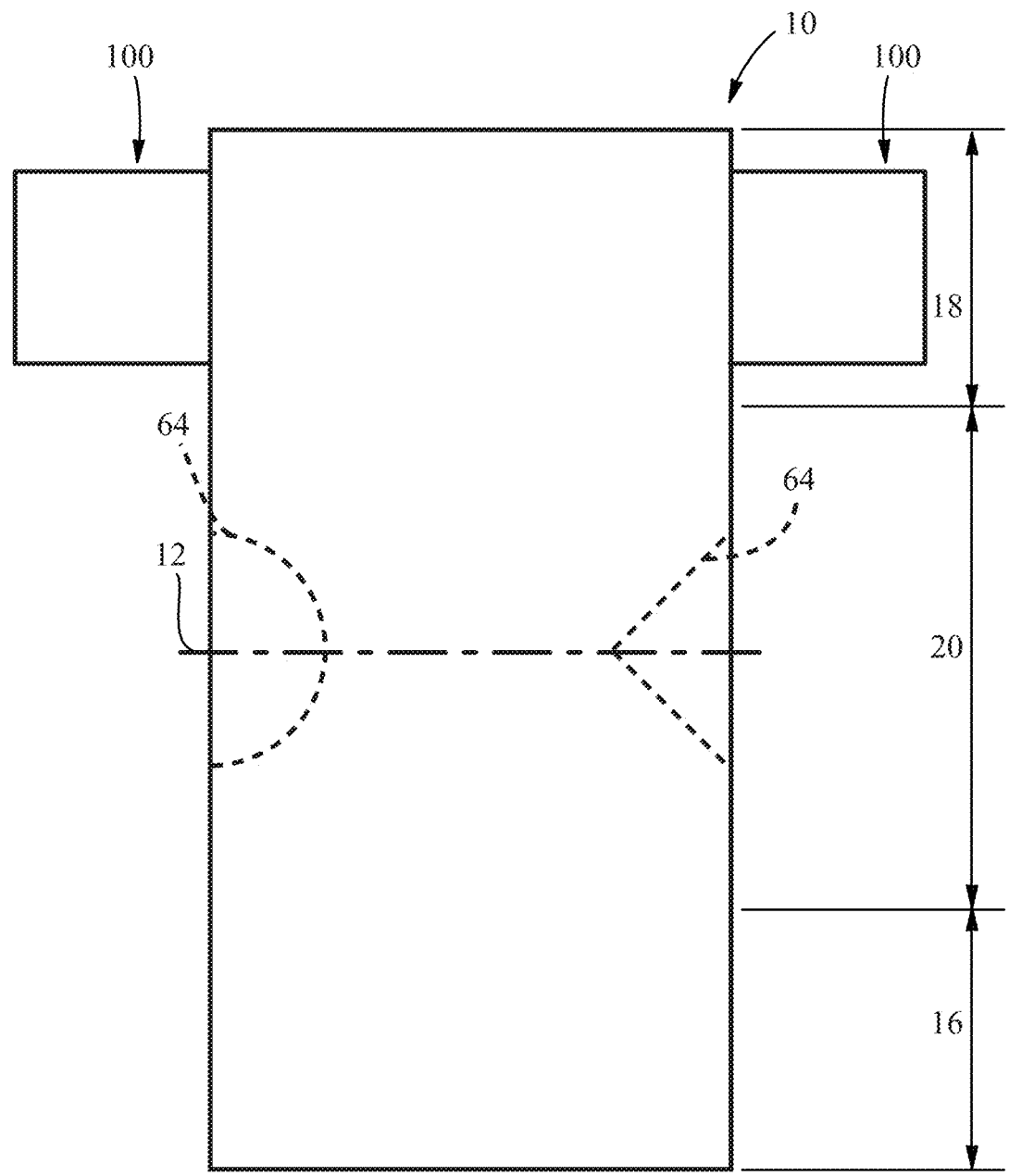
FIG. 10 is a plan view of an example absorbent article of the present disclosure illustrating crotch notches.

In some forms, referring to FIG. 10, instead of the crotch narrow joints being provided, crotch notches 64 may be cut out of the absorbent articles 10, absorbent cores 40 thereof, and/or other components thereof (e.g., acquisition material 50) in areas proximate to the lateral axis 12. In other forms, the crotch notches 64 may instead be formed in components of the absorbent articles before or during manufacture. The crotch notches 64 may have any suitable size and shape to achieve a narrow folded crotch width. Some example shapes are illustrated in FIG. 10. The crotch notches 64 may be formed in the topsheet, the backsheet, the acquisition material, the outer cover nonwoven material, and/or portions of the cuffs, for example. The crotch notches 64 may be used with the hourglass or extended hourglass shaped absorbent cores disclosed herein. The acquisition material 50 and/or distribution material may also be hourglass shaped, for example. The crotch notches 64 may be cut out so that a chassis of the absorbent article is hourglass shaped, or has an extended (along the longitudinal axis 14) hourglass shape.

Figure 9A:
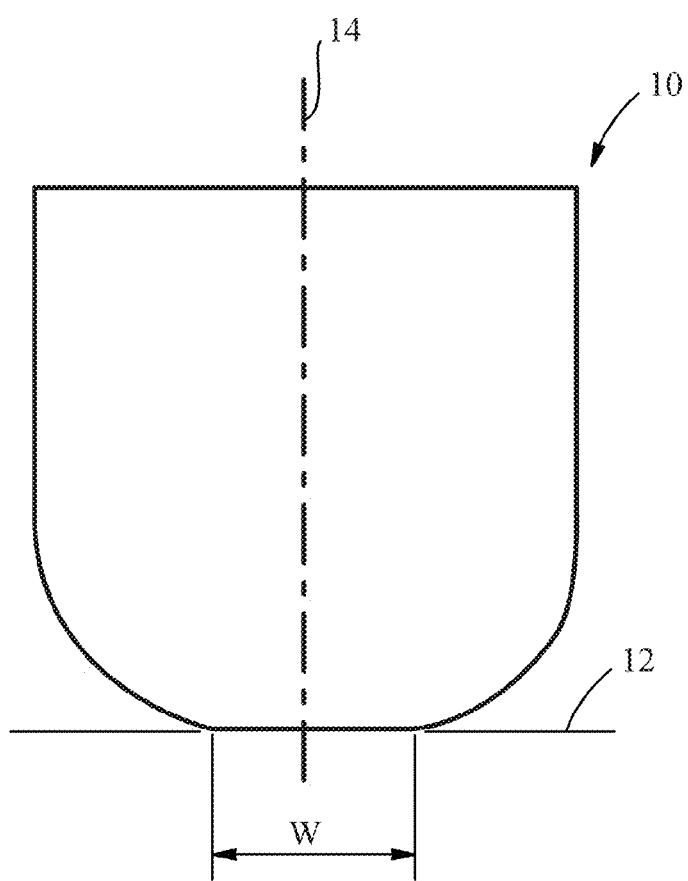
FIG. 9A is a plan view of an example absorbent of the present disclosure.

The crotch narrowing joints 60 may be an optional feature. It has been discovered that a narrow Folded Crotch Width, in some instances, may still be achieved even without the crotch narrowing joints 60. This narrow Folded Crotch Width may be attributable to the elongated hourglass shapes of the absorbent core (see FIG. 5) in combination with elastic contraction from at least one pair of leg cuffs 26, and possibly from two pairs of leg cuffs 26 and 27. In such an instance, the absorbent article, in a folded configuration, may take on the example shape of FIG. 9A. FIG. 9A illustrates the narrow Folded Crotch Width as "W".

The folded crotch width, (i.e., W in FIG. 1) measured according to the Folded Crotch Width Test herein, may be less than about 150 mm, less than about 100 mm, less than about 75 mm, less than about 50 mm, less than about 45 mm, less than about 50 mm, less than about 40 mm, less than about 35 mm, less than about 30 mm, less than about 25 mm, less than about 20 mm, or less than about 15 mm, depending on the size of the absorbent article 10. The folded crotch width, measured according to the Folded Crotch Width Test herein, may be in the range of about 10 mm to about 150 mm, about 10 mm to about 100 mm, about 10 mm to about 75 mm, about 15 mm to about 50 mm, about 15 mm to about 45 mm, less than 45 mm, less than 40 mm, less than 35 mm, about 20 mm to about 40 mm, about 25 mm to about 35 mm, or about 15 mm to about 30 mm, for example, specifically reciting all 0.1 mm increments within the above-specified ranges and all ranges formed therein or thereby.

As discussed above, referring to FIGS. 2, 4, 6, and 11, one or more wetness guards 22, 24 may be provided on the absorbent article 10. In general, the wetness guards 22 and 24 are provided to establish a barrier between the lower back, waist, and/or legs of the baby and portions of the topsheet 36 that are soiled with bodily exudates. A first wetness guard 22 may be positioned on the first side of the central lateral axis 12 and a second wetness guard 24 may be positioned on the second side of the central lateral axis 12. As mentioned previously, only one wetness guard (either 22 or 24) may be provided in certain absorbent articles 10. In some forms, other wetness guards may also be provided either in addition to the wetness guards 22 and 24, or in lieu of them. As an example, some wetness guards may extend longitudinally at least partially between the first end edge 28 and the second end edge 30. The wetness guards 22 and 24 may have any suitable width (measured in a direction parallel to the central lateral axis 12) and the length (measured in a direction parallel to the central longitudinal axis 14). In some instances, the wetness guards 22 and 24 may have a first width and the absorbent articles 10 may have a second width. The first width may be the same as or different than (larger or smaller) than the second width. For example, a wetness guard may only extend intermediate the cuffs 26 or the cuffs 27 and not extend all the way to the first and second side edges 32 and 34. In some instances, one of the wetness guards 22 or 24 may have a first width and the other of the wetness guards 22 or 24 may have a second width. The first and second widths may be the same or different. In some instances, one of the wetness guards 22 or 24 may have a first length (measured in a parallel to the central longitudinal axis 14) and the other of the wetness guards 22 or 24 may have a second length. The first and second lengths may be the same or different. The first wetness guard 22 may have a longer length than the second wetness guard 24, or vice versa. In some instances, the wetness guards 22 and 24 may have the same length such that the absorbent article 10 may be reversible. The first wetness guard 22 may overlap a first portion of the absorbent core and the second wetness guard 24 may overlap a second portion of the absorbent core.

Figure 11:
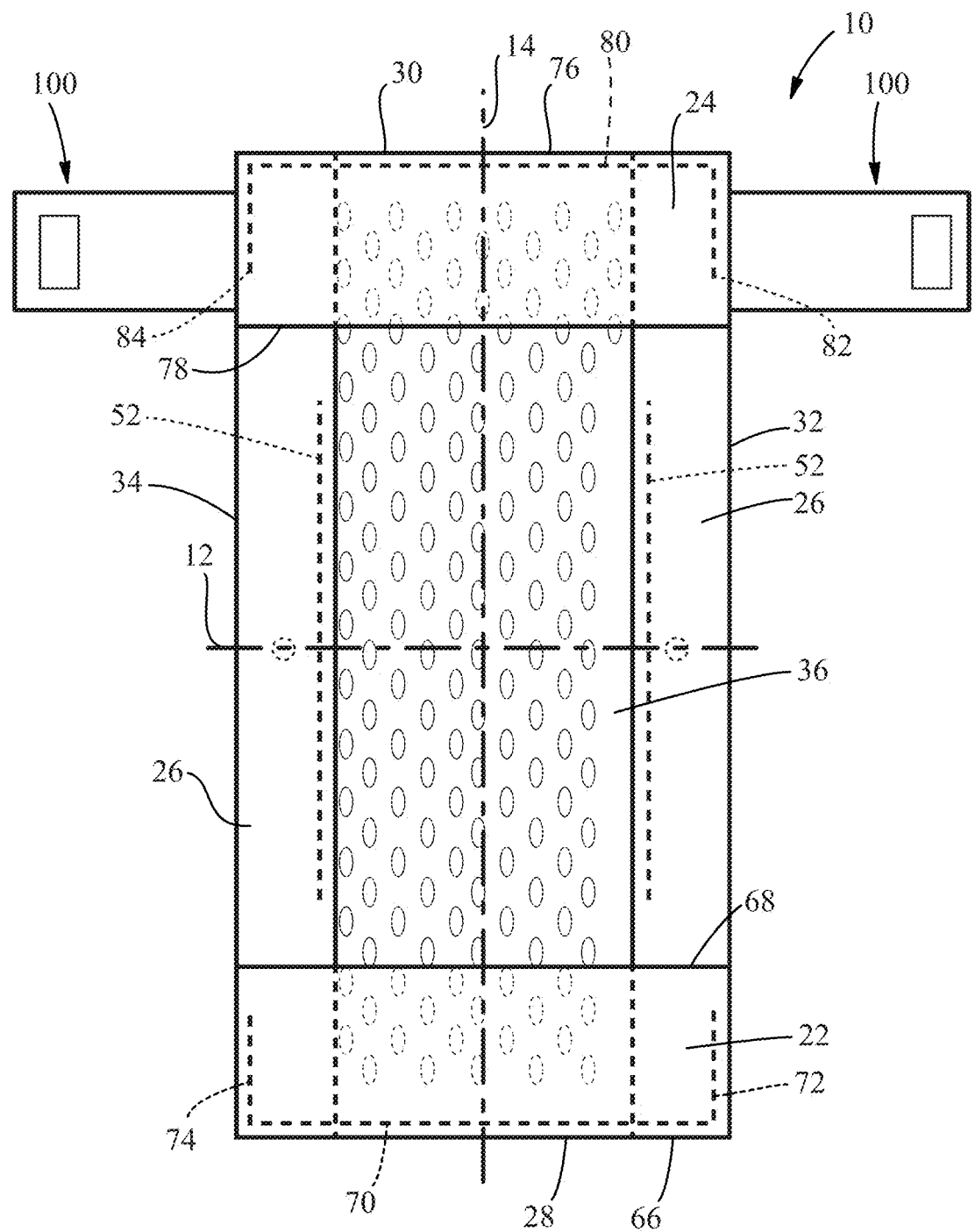
FIG. 11 is a plan view of an example absorbent article of the present disclosure, wearer-facing surface facing the viewer, and comprising two wetness guards.

Referring to FIG. 11, the first wetness guard 22 may have a first end 66 and a second end 68. The first end 66 may be positioned proximate to the first end edge 28 of the absorbent article 10. The second end 68 may be positioned intermediate the first end edge 28 and the lateral axis 12. Although the second end 68 of the first wetness guard 22 is illustrated as being straight, it may also be concave or convex relative to the lateral axis 12 or may have any other suitable shape. The first wetness guard 22 may be positioned over at least a portion of the topsheet 36 and may overlap or cross the longitudinal axis 14. In other instances, the wetness guard 22 may be positioned over a portion of the topsheet 36 and portions of the cuffs 26, 27 or the raised barriers.

Figure 12:
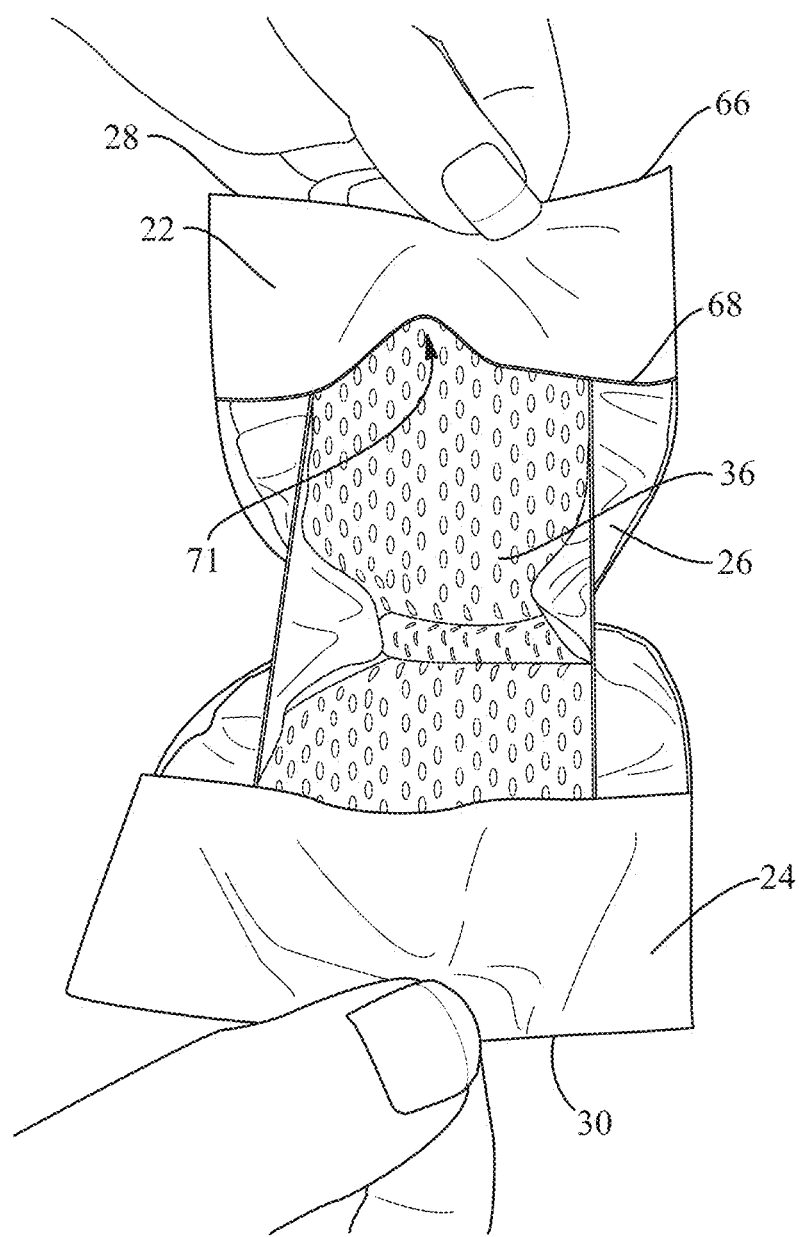
FIG. 12 is a perspective view of an example absorbent article of the present disclosure, wearer-facing surface facing the viewer, and illustrating wetness guards.

Again referring to FIG. 11, a first portion 70 of the first wetness guard 22 may be joined to the cuffs 26, 27, the raised barriers, the topsheet 36, and/or the backsheet 38 proximate to the first end edge 28 of the absorbent article 10. A second portion 72 of the first wetness guard 22 may be joined to the cuffs 26, 27, the raised barriers, the topsheet 36, and/or the backsheet 38 proximate to the first side edge 32 of the absorbent article 10. A third portion 74 of the first wetness guard 22 may be joined to the cuffs 26, 27, the raised barriers, the topsheet 36, and/or the backsheet 38 proximate to the second side edge 34 of the absorbent article 10. The joining may comprise using mechanical joining or adhesive joining, for example. The joining may be intermittent or continuous. Through this joining, referring to FIG. 12, the second end 68 may be free of attachment to the topsheet 36, the cuffs 26, 27, and the raised barrier such that a pocket, 71, is created at least between a non-wearer-facing surface of the first wetness guard 22 and the topsheet 36. In other instances, the second end 68 may be joined to, or partially joined to, the topsheet 36, the cuffs 26, 27, and/or the raised barriers, for example. A pocket may also be created by the second wetness guard 24 in a similar fashion as the pocket 71 of the wetness guard 22.

Still referring to FIG. 11, the second wetness guard 24 may have a first end 76 and a second end 78. The first end 76 may be positioned proximate to the second end edge 30 of the absorbent article 10. The second end 78 may be positioned intermediate the second end edge 30 and the lateral axis 12. Although the second end 78 of the second wetness guard 24 is illustrated as being straight, it may also be concave or convex relative to the lateral axis 12 or may have any other suitable shape. The second wetness guard 24 may be positioned over at least a portion of the topsheet 36 and may overlap or cross the longitudinal axis 14. In other instances, the wetness guard 24 may be positioned over the portion of the topsheet 36 and portions of the cuffs 26, 27 or the raised barriers.

A first portion 80 of the second wetness guard 24 may be joined to the cuffs 26, 27, the raised barriers 56, the topsheet 36, and/or the backsheet 38 proximate to the second end edge 30 of the absorbent article 10. A second portion 82 of the second wetness guard 24 may be joined to the cuffs 26, 27, the raised barriers, the topsheet 36, and/or the backsheet 38 proximate to the first side edge 32 of the absorbent article 10. A third portion 84 of the second wetness guard 22 may be joined to the cuffs 26, 27, the raised barriers, the topsheet 36, and/or the backsheet 38 proximate to the second side edge 34 of the absorbent article 10. The joining may comprise using mechanical joining or adhesive joining, for example. The joining may be intermittent or continuous. Through this joining, the second end 78 may be free of attachment to the topsheet 36, the cuffs 26, 27, and the raised barrier, such that a pocket (like pocket 71 of FIG. 12) is created at least between a non-wearer-facing surface of the second wetness guard 24 and the topsheet 36. In other instances, the second end 78 may be joined to, or partially joined to, the topsheet 36, the cuffs 26, 27, and/or the raised barriers, for example.

In other instances, the first and/or the second wetness guards 22 and 24 may be joined to the topsheet 36, the cuffs 26, 27, the raised barriers, and/or the backsheet 38 at any suitable locations on a wearer-facing surface of the absorbent article 10. In an instance, all, or some of the perimeters of the wetness guards 22 and 24 may be joined to the wearer-facing surface. In other instances, all or some of non-perimeter areas may be joined to the wearer-facing surface. The two wetness guards 22 and 24, if both are provided, may be joined to a portion of the wearer-facing surface in the same fashion or in different fashions. In an instance, one or both of the wetness guards 22 and 24 may be discrete components that are not joined to the absorbent article 10 in a package, but instead are provided as a discrete component. Nurses or caregivers may then position the wetness guard or guards on portions of the wearer-facing surface of the absorbent articles 10 as appropriate. The wetness guards 22 and 24 may have a space between themselves and the first and second end edges 28 and 30. Stated another way, the most longitudinally outward portions of each wetness guard does not have to be positioned on the first end edges 28 or the second end edge 30, but instead a gap may exist, such as a 0.5 inch gap, for example.

The wetness guards 22 and 24 may have the same construction or a different construction. Referring to FIGS. 2 and 4, the wetness guard 22 and 24 may each comprise a laminate comprising a first liquid impermeable material (or substantially liquid impermeable material) 86 and a second liquid permeable material 88. The wetness guards may also comprise other liquid permeable or impermeable layers. The layers 86 and 88 may be joined together in any suitable fashion, such as through the use of an adhesive 90. The adhesive 90 may be continuous or discontinuous and may be slot coated or spirally applied, for example. The first liquid impermeable material 86 may comprise one or more nonwoven materials or films or a nonwoven and a film as a laminate. The second liquid permeable material 88 may comprise one or more nonwoven materials or non-film materials. The first liquid impermeable material 86 may face a portion of the topsheet 36, while the second liquid permeable material 88 may face the wearer or form a portion of a wearer-facing surface of the absorbent article. As such, the first liquid impermeable material 86 may be used to create a barrier between the portion of the topsheet 36 under the wetness guards and the second liquid permeable material 88 to keep material 88 dry and sterile. The second liquid permeable material 88 may be used to provide a lower back, waist, and/or legs of a baby with a soft, dry, sterile, and comforting surface. In an instance, the wetness guards 22 and 24 may comprise only one or more hydrophobic nonwoven materials without a liquid impermeable film. The hydrophobic nonwoven material(s) may be untreated, such that it remains naturally hydrophobic. In other instances, the hydrophobic nonwoven material(s) may be treated to become more hydrophobic.

The first and second wetness guards 22 and 24 may form a crotch receiving area 92 in the absorbent article 10. The crotch receiving area 92 is the area between the two wetness guards 22 and 24 where a baby's crotch area is positioned when the absorbent article 10 is positioned on the baby. The crotch receiving area 92 between the first and second wetness guards 22 and 24 may be any suitable size (length or width) for a particular size baby. A ratio of the surface area of the crotch receiving area 92 to the wetness guards 22 and 24 (together or separate if only one is provided) may be about 7:1, about 6:1, about 5:1, about 4:1, about 3:1, about 2:1, about 1:1, or about 0.5:1, or may be in the range of about 10:1 to about 1:1, specifically reciting all 0.1 increments of the ratios specified above and all ratios formed within the specified range. The crotch receiving area 92 may have an area in the range of about 25 cm$^2$ to about 750 cm$^2$, about 40 cm$^2$ to about 500 cm$^2$, about 50 cm$^2$ to about 400 cm$^2$, about 50 cm$^2$ to about 250 cm$^2$, about 50 cm$^2$ to about 200 cm$^2$, about 50 cm$^2$ to about 150 cm$^2$, about 50 cm$^2$ to about 100 cm$^2$, or about 60 cm$^2$ to about 80 cm$^2$, for example, specifically reciting all 0.1 cm$^2$ increments within the specified ranges and all ranges formed therein or thereby.

The absorbent article, when laid flat, elastic contraction pulled out, may have a length, in a direction parallel to a central longitudinal axis 14, of less than 500 mm, less than 400 mm, less than 300 mm, less than 275 mm, but at least 100 mm. The absorbent article, when laid flat, elastic contraction pulled out, may have a width, in a direction parallel to a central lateral axis 12 of less than 200 mm, less than 150 mm, less than 130 mm, less than 100 mm, but at least 50 mm.

To create the first and/or second wetness guards 22 and 24, the backsheet 38 and the outer cover nonwoven material 58 may extend beyond the first and second end edges 28 and 30 and be folded over the wearer-facing side of the absorbent article 10. The folded over portions of the backsheet 38 and the outer cover nonwoven 58 may be joined to the topsheet 36, portions of the cuffs 26, 27, the raised barriers, and/or the backsheet 38. As such, the folded over portion of the backsheet 38 may form the first liquid impermeable material 86 and the outer cover nonwoven material 58 may form the second liquid permeable material 88 of the wetness guards 22 and 24. In other instances, the backsheet 38 and the outer cover nonwoven material 58 may not be joined to a portion of the wearer-facing surface, but instead may merely be folded over the wearer-facing surface.

In another instance, the first and/or second wetness guards 22 and 24 may be formed from discrete laminates each comprising the first liquid impermeable material 86 and the second liquid impermeable material 88. These discrete laminates may be joined to the topsheet 36, portions of the cuffs 26, 27, portions of the raised barriers, and/or to the backsheet 38.

The absorbent article 10 may have a wearer-facing surface area (the entire wearer-facing surface including areas of the wetness guards) in the range of about 150 $cm^2$ to about 1,500 $cm^2$, about 175 $cm^2$ to about 1,000 $cm^2$, about 200 $cm^2$ to about 800 $cm^2$, about 200 $cm^2$ to about 500 $cm^2$, about 200 $cm^2$ to about 400 $cm^2$, about 200 $cm^2$ to about 300 $cm^2$, about 200 $cm^2$ to about 250 $cm^2$, about 210 $cm^2$ to about 240 $cm^2$, or about 225 $cm^2$, for example, specifically reciting all 0.1 $cm^2$ increments within the specified ranges and all ranges formed therein or thereby.

The wetness guards 22 or 24 may have an area in the range of about 10 $cm^2$ to about 800 $cm^2$, about 15 $cm^2$ to about 600 $cm^2$, about 15 $cm^2$ to about 400 $cm^2$, about 20 $cm^2$ to about 300 $cm^2$, about 20 $cm^2$ to about 200 $cm^2$, about 20 $cm^2$ to about 100 $cm^2$, about 20 $cm^2$ to about 75 $cm^2$, or about 25 $cm^2$ to about 70 $cm^2$, for example, specifically reciting all 0.1 $cm^2$ increments within the specified ranges and all ranges formed therein or thereby. As mentioned above, the wetness guard 22 may have an area that is the same or different than the wetness guard 24, if both are provided in an absorbent article.

Figure 13:
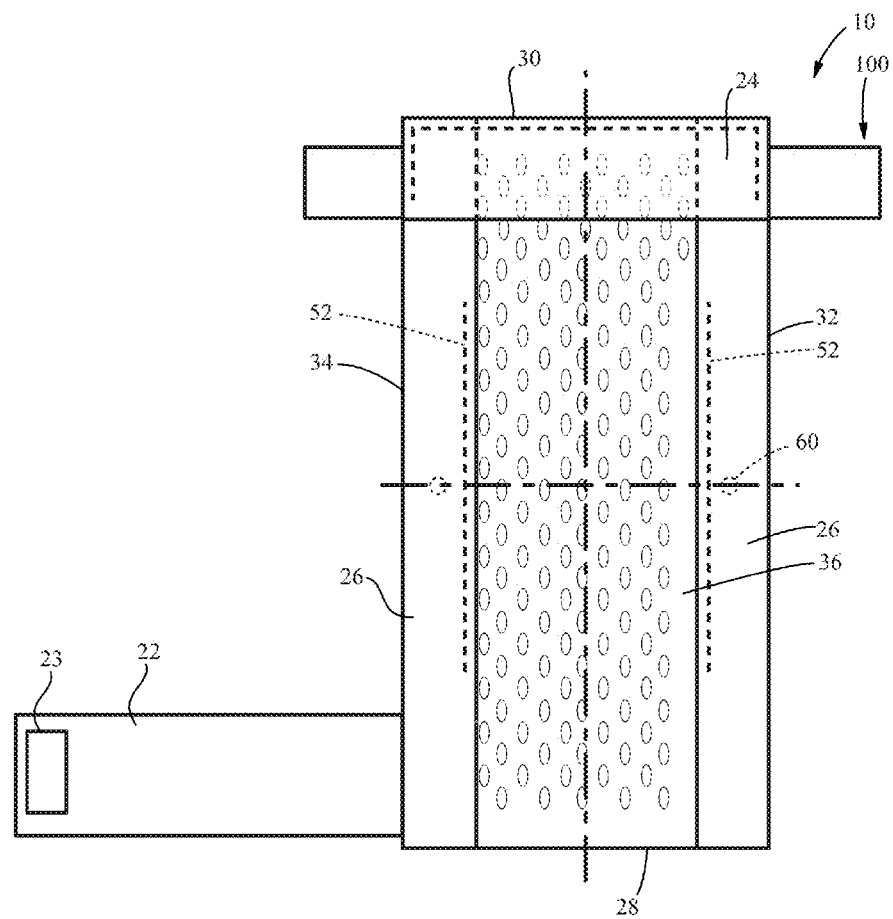
FIG. 13 a is plan view of an example absorbent article of the present disclosure, wearer-facing surface facing the viewer, and illustrating two wetness guard configurations.

In another instance, referring to FIG. 13, at least one of or both of the wetness guards 22 and 24 may only be attached to the first side edge 32, the second side edge 34, and/or a portion of the absorbent article 10 proximate to one of the side edges 32 and 34, for example. In other instances, the wetness guards 22 and/or 24 may be attached to the outer cover nonwoven material 58, the backsheet 38, the topsheet 34, one of the raised barriers, and/or one of the cuffs (26 or 27), for example. In such an instance, the wetness guard 22 in FIG. 13 may be configured to be folded over into the position illustrated in, for example FIG. 2. The wetness guard 24 may have a similar configuration as the illustrated wetness guard 22 or may be provided as described with reference to FIG. 2. The wetness guard 22 (and/or the wetness guard 24 if provided in the same configuration) may comprise a fastener 23, such as a plurality of hooks or an adhesive, for example, such that when the wetness guard 22 is folded over the absorbent article 10, it can be joined by the fastener 23 to a portion of the wearer-facing surface of the absorbent article 10. The materials of the wetness guard 22 may be the same as or similar to that described above.

Figure 14:
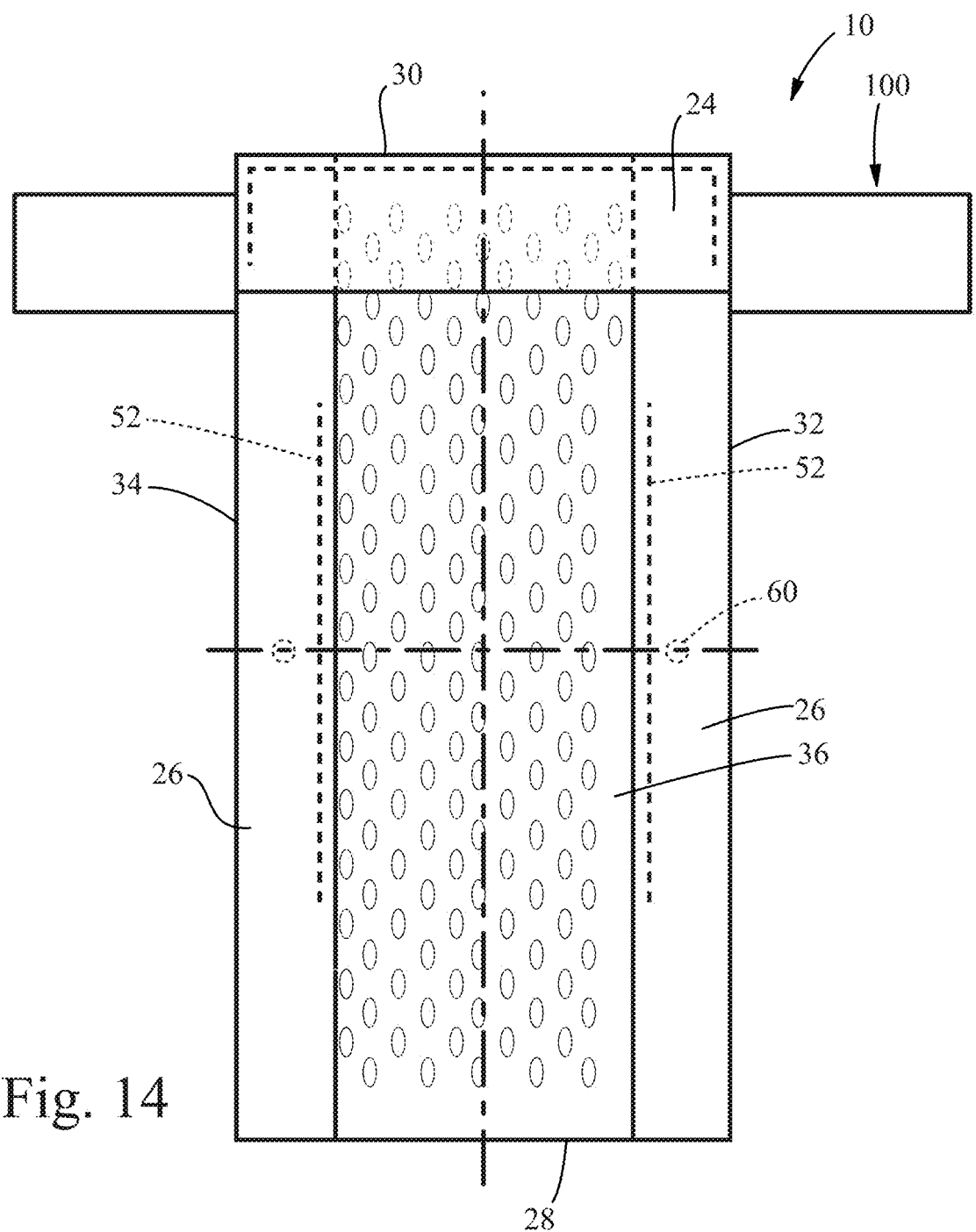
FIG. 14 is a plan view of an example absorbent article of the present disclosure, wearer-facing surface facing the viewer, and illustrating two wetness guard configurations.
Figure 15:
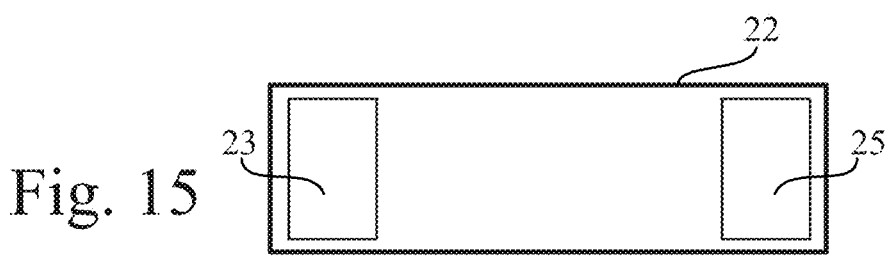
FIG. 15 is a plan view of an example discrete wetness guard for use with the absorbent article of FIG. 14.

In still other instances, referring to FIGS. 14 and 15, one or both of the wetness guards 22 and 24 may be a discrete component (FIG. 15) from the absorbent article 10 (FIG. 14) and may be configured to be placed on the absorbent article 10, in for example, the positions illustrated in FIG. 2, or in other positions as desired by the nurse or caregiver. In some instances, as illustrated in FIGS. 14 and 15, one wetness guard 22 may be a discrete component and the other wetness guard 24 may be joined to the cuffs 26 (or 27), the raised barrier, the topsheet 36, and/or the backsheet 38. The discrete wetness guard or guards may be packaged with the absorbent articles 10 or may be packaged and/or sold separately. The discrete wetness guard 22 (and/or the wetness guard 24, if discrete) may have a first fastener 23 and a second fastener 25. The first and second fasteners 23 and 25 may be used to join the discrete wetness guard 22 to a portion of the wearer-facing surface of the absorbent article 10 as desired and maintain the wetness guard 22 in position during use of the absorbent article 10. The materials of the wetness guard may be the same as or similar to that described above.

Figure 16:
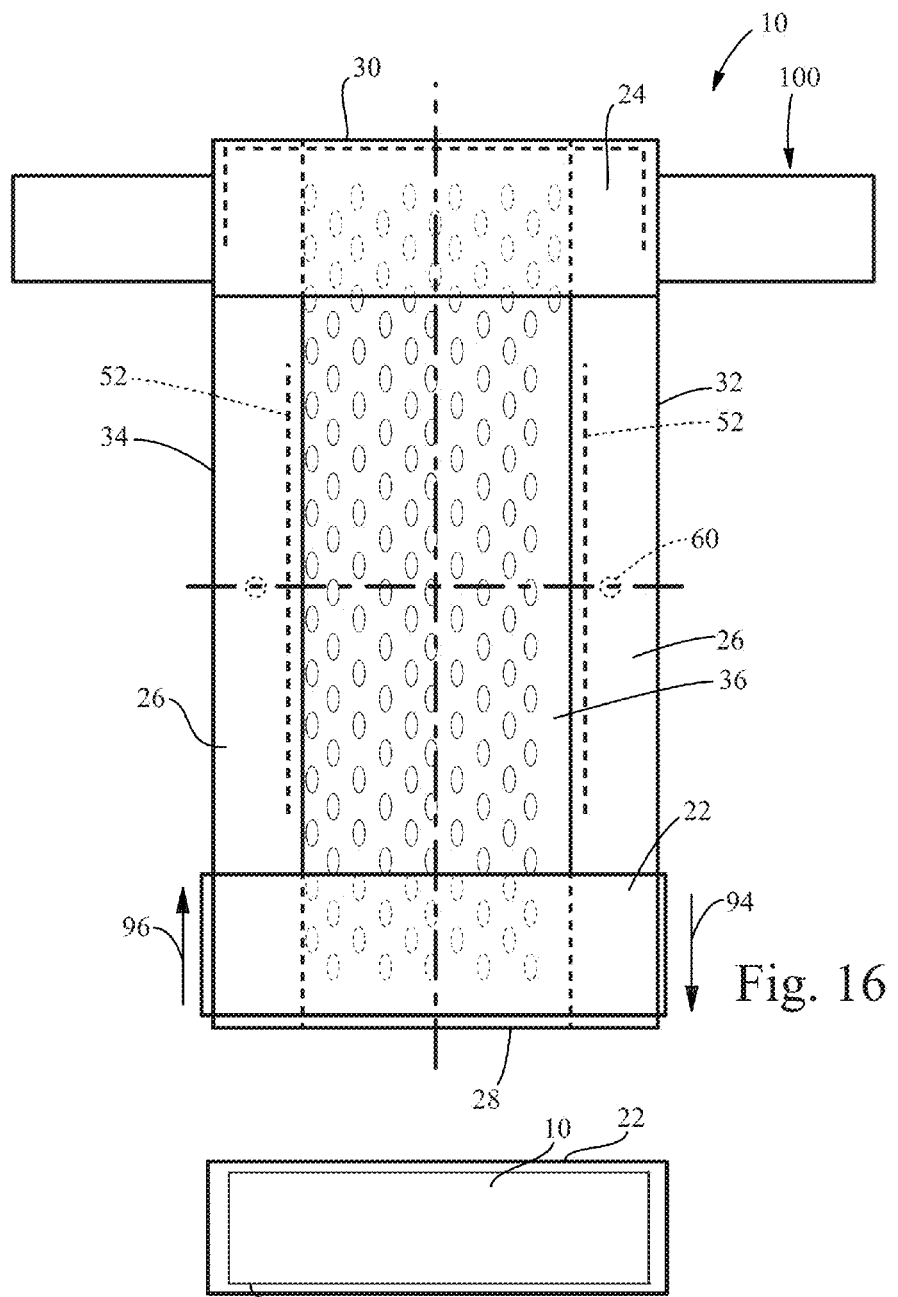
FIG. 16 is a plan view of an example absorbent article of the present disclosure, wearer-facing surface facing the viewer, and illustrating two wetness guard configurations.
Figure 17:
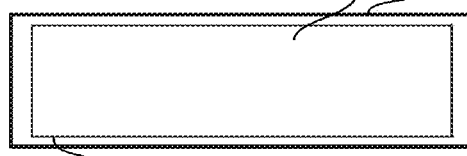
FIG. 17 is a schematic illustration of how the sleeve type wetness guard of FIG. 16 would surround a portion of an absorbent article.

In yet other instances, referring to FIGS. 16 and 17, at least one of, or both of, the wetness guards 22 and 24 may be provided in a sleeve form. The sleeve may be positioned on the absorbent article 10 in a package, positioned separately from the absorbent article 10 in the package, or may be sold in a separate package. Once positioned on the absorbent article, the sleeve may be moveable in the directions of arrows 94 and 96 to allow a nurse or caregiver to position the wetness guard 22 as desired. In some instances, as illustrated in FIG. 16, one wetness guard 24 may be joined to the wearer-facing surface and another wetness guard 22 may take the form of a sleeve. In some forms, the materials of the wetness guard may be the same as or similar to that described above. In other forms, only portions of the wetness guard positioned over the wearer-facing surface may have the wetness guard constructions described herein, with other portions (i.e., portions wrapped around a non-wearer-facing surface 98 of the absorbent article 10) being constructed of other materials, such as nonwoven materials without films, for example. FIG. 17 illustrates an example of how the wetness guard 22 in the form of a sleeve would surround the absorbent article 10.

Figure 18:
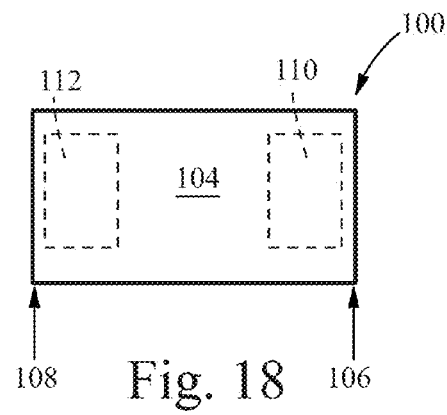
FIG. 18 is a plan view of an example of a discrete fastening member for an absorbent article of the present disclosure, garment-facing surface facing the viewer.
Figure 19:
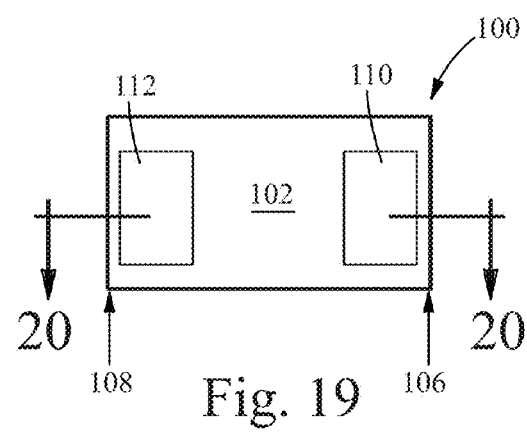
FIG. 19 is a plan view of an example of a discrete fastening member for an absorbent article of the present disclosure, wearer-facing surface facing the viewer.

The absorbent articles 10 of the present disclosure may have one or more fastening members. The fastening members may be related art fastening members (i.e., taped fastening members) that are permanently attached to the absorbent article 10 in the back waist region 18 and are engaged by fasteners (e.g., hooks) to a garment-facing surface of the front waist region or vice versa. In some instances, a landing zone may be provided on the garment-facing surface of the front waist region 16 for such engagement. In other instances the fastening members may be fully removable fastening members 100. The fastening members may be stretch panels that may be discrete elements. Referring to FIGS. 18 and 19, the fastening members 100 may each comprise a first surface 102, a second surface 104, a first end 106, and a second end 108. The first surface 102 may be opposite to the second surface 104 and the first end 106 may be opposite to the second end 108. The fastening members 100 may comprise a first fastener 110 configured to engage a first portion of the outer cover nonwoven material 58 or a first portion of a landing zone and positioned on the first surface 102. The absorbent article 10 may be free of a landing zone. The fastening members 100 may comprise a second fastener 112 configured to engage a second, different portion of the outer cover nonwoven material 58 and positioned on the first surface 102. In some instances, it may be desirable to provide the first fastening member 110 on the first surface 102 and the second fastening member 112 on the second surface 104, so that the fastener can be folded into a loop to hold a tube, for example. The first portion of the outer cover nonwoven material 58 may be in the front waist region 16, the back waist region 18, or the crotch region 20. Likewise, the second portion of the outer cover nonwoven material 58 may be in the front waist region 16, the back waist region 18, or the crotch region 20. The fastener 110 may be positioned proximate to the first end 106 and the fastener 112 may be positioned proximate to the second end 108. In some instances, only one fully removable fastening member 100 may be provided on an absorbent article 10 and the other fastening member may be permanently joined to the absorbent article on at least one of its ends.

Since the fastening members 100 are removable from the absorbent article 10, they can be fastened as desired or as needed by a nurse or caregiver. In some instances, the nurse or caregiver may remove the fastening members 100 from the absorbent article 10 and not use them if the baby is in a certain position, for example. In other instances, the nurse or caregiver may only use one of the fastening members 100 if the baby is in another certain position, for example.

Referring to FIGS. 18-22, the first fastener 110 and the second fastener 112 may not extend to the perimeter of the fastening members 100. This may help prevent, or at least inhibit, rough fastener material (e.g., hooks) from contacting or irritating a wearer's skin. The fasteners 110 and 112 are illustrated as rectangular but may be any other suitable shape, such as circular or ovate, for example. In some instances, it may be desirable to have fasteners without corners to again prevent, or at least inhibit the fasteners from at irritating a wearer's skin. In a package, the first and second fasteners 110 and 112 may be joined to the first surface 102 so they are at least inhibited from unintentionally engaging other portions of the absorbent pads, other fastening members, and/or other items.

Figure 20:
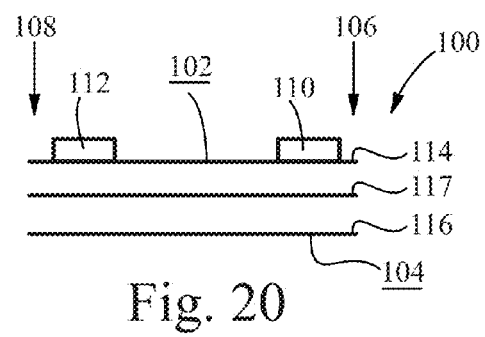
FIG. 20 is a cross-sectional view of the discrete fastening member taken about line 20-20 of FIG. 19.

Referring to FIG. 20, the fastening members 100 may comprise a first nonwoven or other substrate 114, a second or other nonwoven substrate 116, and an elastic material 117 positioned at least partially intermediate the first and second substrates 114 and 116. The elastic material may comprise an elastic nonwoven material, an elastic film, or elastic strands, for example. The elastic material may be apertured or micro-apertured to promote breathability. In other instances, the fastening members may comprise one or more substrates and may not comprise an elastic material.

Figure 21:
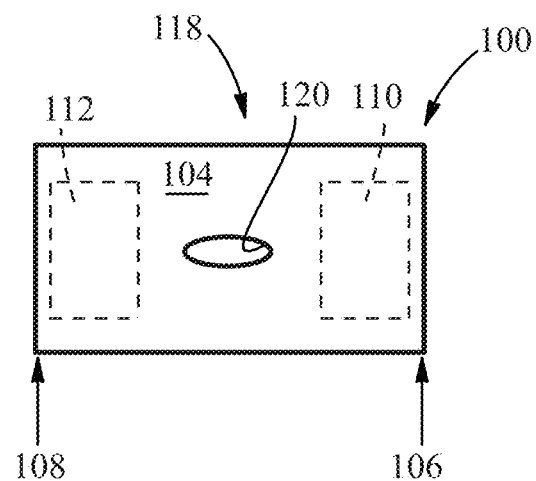
FIG. 21 is a plan view of an example of a discrete fastening member for an absorbent article of the present disclosure, garment-facing surface facing the viewer.
Figure 22:
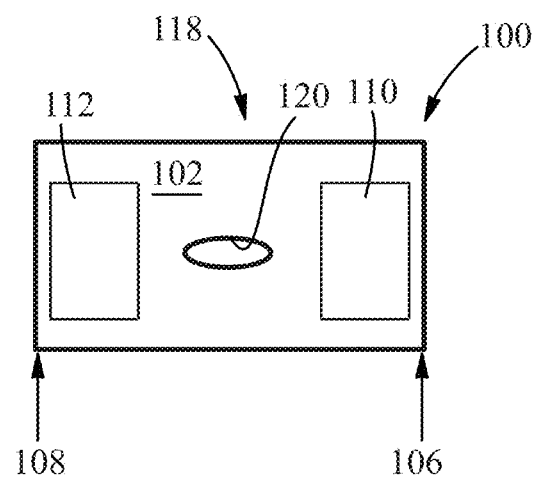
FIG. 22 is a plan view of an example of a discrete fastening member for an absorbent article of the present disclosure, wearer-facing surface facing the viewer.

Referring to FIGS. 21 and 22, a middle portion 118 (e.g., between the first and second ends 106 and 108) of the fastening member 100 may define one or more slots 120 or apertures therein. The slots or apertures 120 may have any suitable size and/or shape. In certain instances, premature, NAS babies, and other babies are on feeding tubes, corded monitoring device (e.g., heart rate monitor), corded life support device, or the like. These tubes and cords may be positioned through the slots 120 or apertures to help hold the tubes and cords in place. In some instances, the middle portion 118, or other portions, of the fastening member 100 may be formed of a highly breathable material, such as a highly breathable film, nonwoven, film/nonwoven laminate, or an apertured film or apertured nonwoven material, for example.

Figure 23:
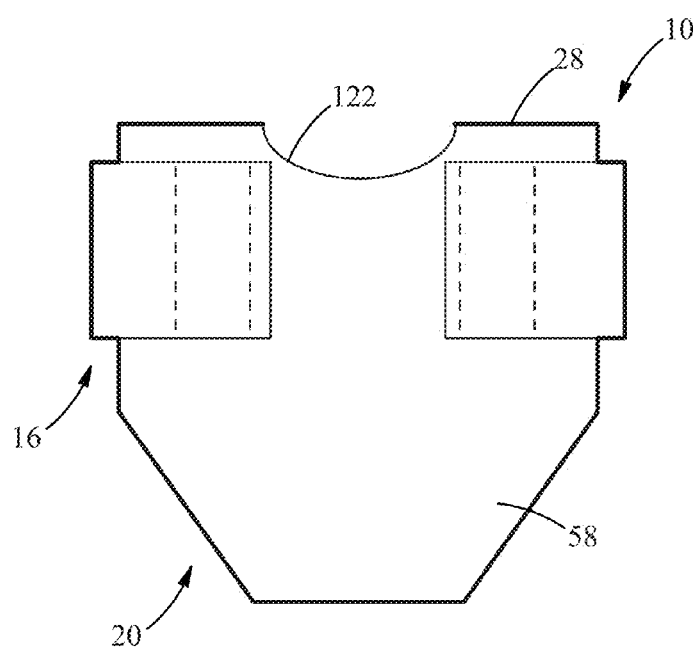
FIG. 23 is a plan view of an example absorbent article of the present disclosure having umbilical cord notches.
Figure 24:
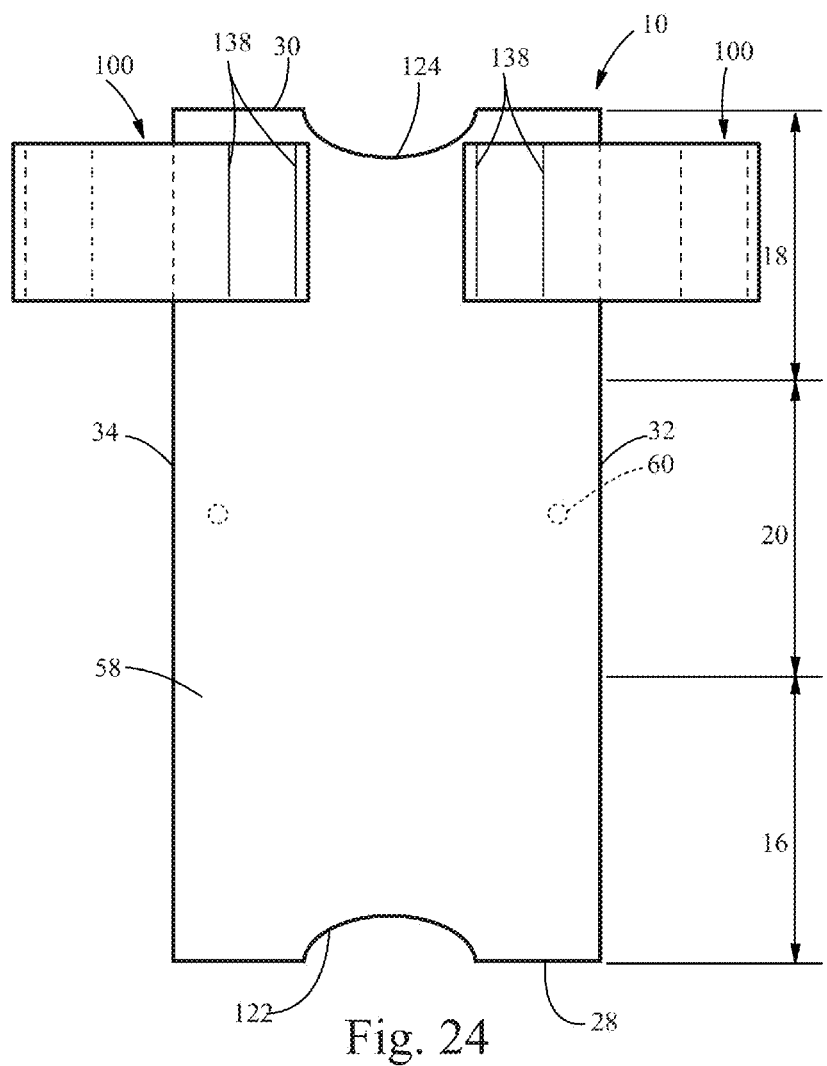
FIG. 24 is a plan view of the example absorbent article of FIG. 23, garment-facing surface facing the viewer.

In some countries, it may be desirable to allow air to flow to the belly button area after birth when a portion of the umbilical cord on the baby is drying out and/or healing. Referring to FIGS. 23 and 24, a first umbilical cord notch 122 may be defined in the first end edge 28 in the front waist region 16 and a second umbilical cord notch 124 may be defined in the second end edge 30 in the back waist region 18. The first and second umbilical cord notches 122 and 124 may have any suitable size, shape, and/or depth relative to the first and second end edges 28 and 30, respectively. In some instances, only the first or the second umbilical cord notch may be provided. The benefit of having two umbilical cord notches is that the absorbent article 10 may be applied with the front waist region 16 on a front of a wearer or with the front waist region 16 on a back of the wearer. Stated another way, by providing the two umbilical cord notches, the absorbent article 10 may be reversible. The longitudinal axis 14 (see e.g., FIG. 2) may extend through the umbilical cord notches.

Referring to FIG. 24, first sides of the fastening members 100 may be permanently fixed to a portion of the back waist region 18 and may not be releasably joined to the absorbent article 10. The first side of the fastening members 100 may be permanently fixed to the portions of the back waist region 18 using one or more bonds 138, lines of adhesives, or may be otherwise permanently fixed. Second sides of the fastening members 100 may comprise fasteners used to join the second sides of the fastening member 100 to portion of the front waist region 16. Alternatively, the second sides of the fastening members 100 may be permanently fixed to the front waist region 16 and the first sides of the fastening members 100 may comprise fasteners used to join the first sides of the fastening members 100 to the back waist region 18.

Figure 25:
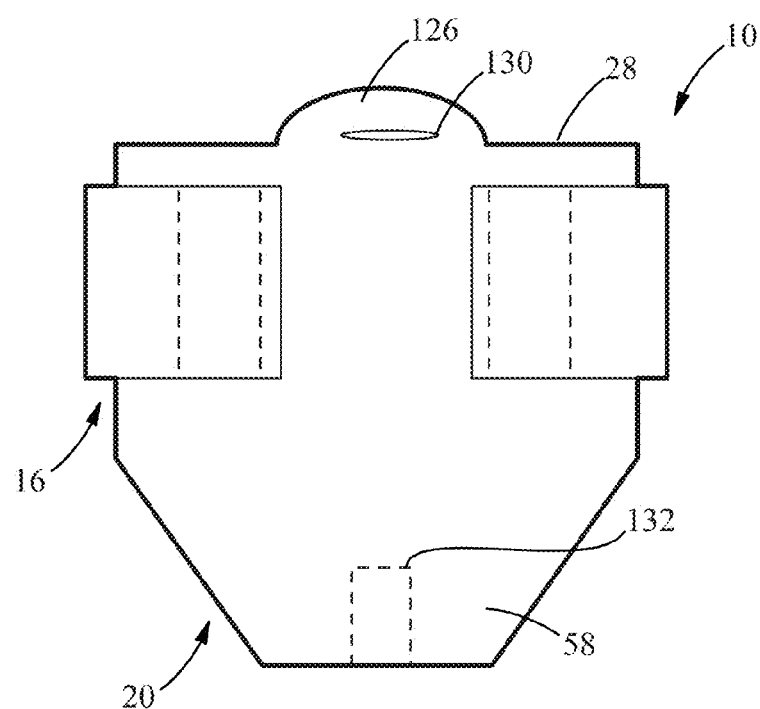
FIG. 25 is a plan view of an example absorbent article of the present disclosure having umbilical cord projections.
Figure 26:
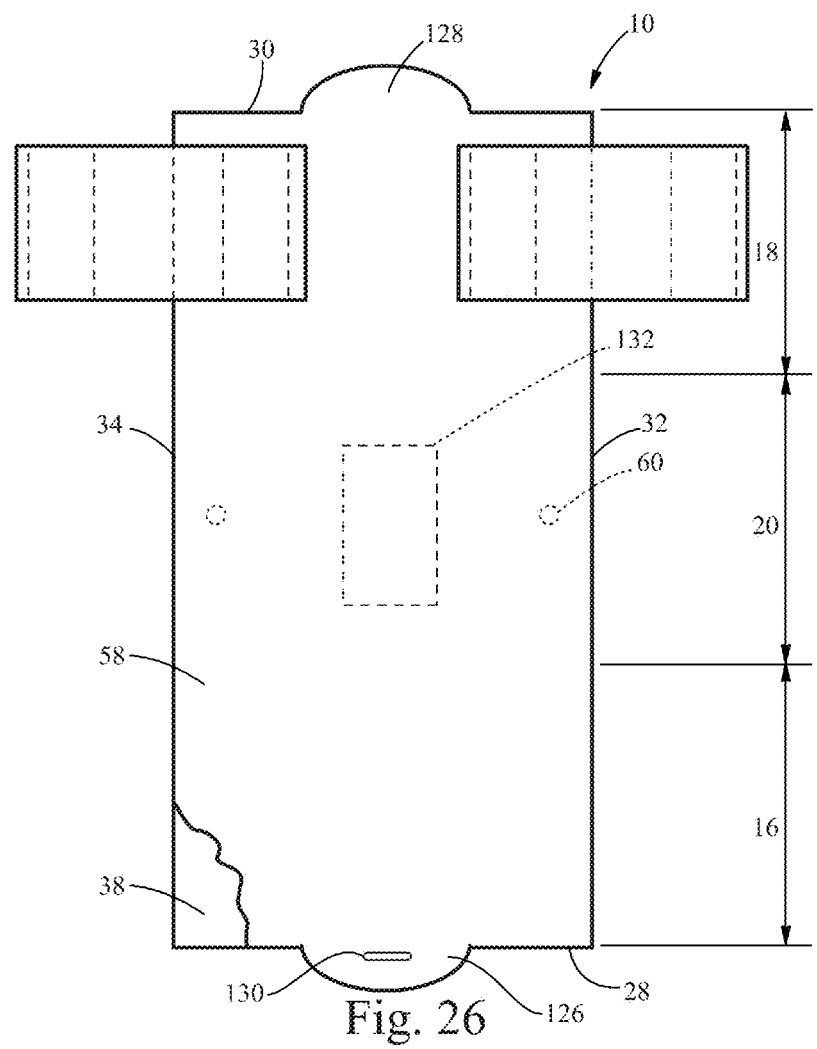
FIG. 26 is a plan view of the example absorbent article of FIG. 25, garment-facing surface facing the viewer.

In some countries, it may be desirable to cover up the belly button of a baby after birth. Referring to FIGS. 25 and 26, a first umbilical cord projection 126 may extend from the first end edge 28 in the front waist region 16 and a second umbilical cord projection 128 may extend from the second end edge 30 in the back waist region 18. The first and second umbilical cord projections 126 and 128 may have any suitable size, shape, and/or height relative to the first and second end edges 28 and 30, respectively. In some instances, only the first or the second umbilical cord projection may be provided. The benefit of having two umbilical cord projections is that the absorbent article 10 may be applied with the front waist region 16 on a front of a wearer or with the front waist region 16 on a back of the wearer. Stated another way, by providing the two umbilical cord projections, the absorbent article 10 may be reversible. The longitudinal axis 14 (see e.g., FIG. 2) may extend through the umbilical cord projections.

The umbilical cord projections may have one or more slots 130 or apertures defined therein. The slots 130 or apertures may have any suitable size and/or shape. In certain instances, premature, NAS babies, and other babies may be on feeding tubes, corded monitoring device (e.g., heart rate monitor), or the like. These tubes and cords may be positioned through the slots 130 or apertures to help hold the tubes and cords in place.

In some instances, no umbilical cord notches or umbilical cord projections may be provided on an absorbent article (see e.g., FIGS. 1 and 2). In still other instances, an umbilical cord notch may be provided on a first side of the lateral axis 12 and an umbilical cord projection may be provided on a second side of the lateral axis 12.

As mentioned above, it may be desirable to reduce contact with premature and NAS babies as much as feasible because of their delicate body and skin. On the other hand, it is also desirable to have the absorbent article on the baby to be as free of bodily exudates as possible to protect the baby's skin. In instances where the babies are positioned in incubators, conventional wetness indicators may not function adequately owing to the high humidity environment of the incubators. The present disclosure provides a way to solve these issues by providing the outer cover nonwoven material 58 and/or the backsheet 38 with a low opacity. By providing the outer cover nonwoven material 58 and/or the backsheet 38 with a low opacity, nurses are able to visually determine, without touching the baby, whether the absorbent articles need to be changed, thus not disturbing the baby if the absorbent article is not soiled or sufficiently soiled.

The opacity of the backsheet 38 may be in the range of about 10% to about 80%, about 15% to about 70%, about 20% to about 70%, or about 25% to about 70%, specifically reciting all 0.1% increments within the specified ranges and all ranges formed therein or thereby. All opacity % are determined using the Opacity Test herein.

The opacity of the outer cover nonwoven material 58 may be in the range of about 1% to about 50%, about 5% to about 30%, about 5% to about 25%, about 10% to about 20%, about 10% to about 15%, or may be less than about 30%, less than about 25%, less than about 20%, less than about 15%, or less than about 10%, specifically reciting all 0.1% increments within the specified ranges and all ranges formed therein or thereby. All opacity % are determined using the Opacity Test herein.

The opacity of both the backsheet 38 and the outer cover nonwoven material 58 measured as a laminate may be in the range of about 15% to about 95%, about 20% to about 80%, about 30% to about 70%, or about 40% to about 60%, specifically reciting all 0.1% increments within the specified ranges and all ranges formed therein or thereby. All opacity percentages are determined using the Opacity Test herein.

Either in addition to or in lieu of the low opacity outer cover nonwoven material 58 and/or the backsheet 38, the absorbent article 10 may comprise a wetness indicator 132, which may be positioned on a wearer-facing side of the backsheet 38 or in other suitable locations. The wetness indicator may be visible from a wearer-facing surface or a garment-facing surface of the absorbent article 10. Thus, as bodily exudates come into contact with the wetness indicator, the wetness indicator may change colors or appear or disappear to indicate to nurses or caregivers that the absorbent article is soiled and needs changed. In other instances, the wetness indicator may change colors, appear, or disappear based on temperature changes (caused by bodily exudates entering the absorbent article) within the absorbent article 10. In other instances, the absorbent article 10 may be free of a wetness indicator.

The absorbent articles 10 may comprise lotions, ointments, skin protecting ointments, vitamins, anti-bacterial treatments, anti-microbial treatments, anti-fungal treatments, on the topsheet 36, leg cuffs 26 and/or 27, and/or other components to promote skin health for the baby.

Package

The absorbent articles of the present disclosure, in their various forms, may be placed into packages. The packages may comprise films, for example. The packages may comprise indicia, brand names, claims, pictures, and/or graphics, relating to the absorbent articles. The absorbent articles within the packages may have all or some of the features disclosed herein. In some instances, the packages may comprise absorbent articles with different features or sizes in the same package or in different packages. As an example, a package may comprise a plurality of absorbent articles and a plurality of discrete fastening members and/or discrete wetness guards configured for use with the absorbent articles. At least some of the plurality of fastening members may each comprise a first surface, a second surface opposite to the first surface, a first end, a second end opposite to the first end, a first fastener comprising a first plurality of hooks on the first surface and positioned proximate to the first end, and a second fastener comprising a second plurality of hooks on the first surface and positioned proximate to the second end.

Arrays

The absorbent articles of the present disclosure may be sold or displaced in arrays or on-line arrays. The arrays or on-line arrays may comprise different sizes of the absorbent articles or absorbent articles with different features. The arrays or on-line arrays may also comprise the discrete fasteners or discrete wetness guards.

Any configurations of the wetness guards 22 and 24 described herein may be used together, for example, a wetness guard that is discrete may be used with a wetness guard that folds over, or a wetness guard that is attached at only one side of the absorbent article 10 may be used with a permanent or discrete wetness guard. Other features of the absorbent articles may be used in combination with any of the wetness guard configurations described herein.

Crotch Compression Force

The absorbent articles of the present disclosure may have a Crotch Compression Force in the range of about 0.4N to about 2.5N, about 0.4N to about 1.5N, about 0.5N to about 2.0N, about 0.6N to about 1.5N, about 0.7N to about 1N, about 0.8N to about 0.9N, about 0.75N to about 1N, or less than about 2.0N, less than about 1.8N, less than about 1.6N, less than about 1.5N, or less than about 1N, specifically reciting all 0.01N increments with the specified ranges and all ranges formed therein or thereby. All Crotch Compression Force measurements are made according to the Crotch Compression Force Measurement Test herein.

Figure 27:
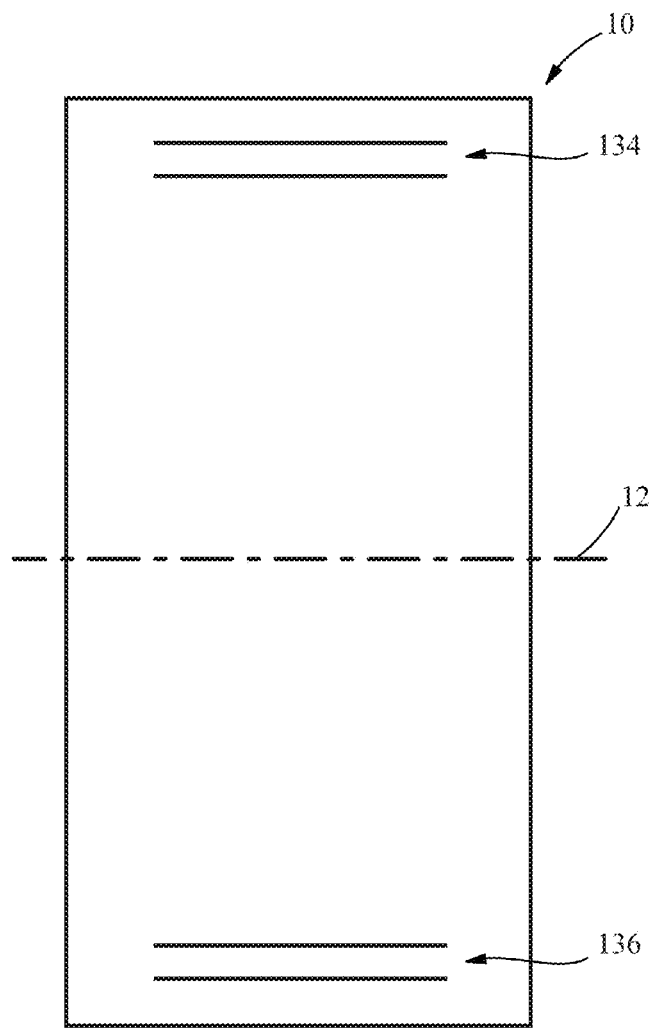
FIGS. 27-29 are schematic illustrations of absorbent articles showing graphics and/or indicia, with their garment-facing surfaces facing the viewer.
Figure 28:
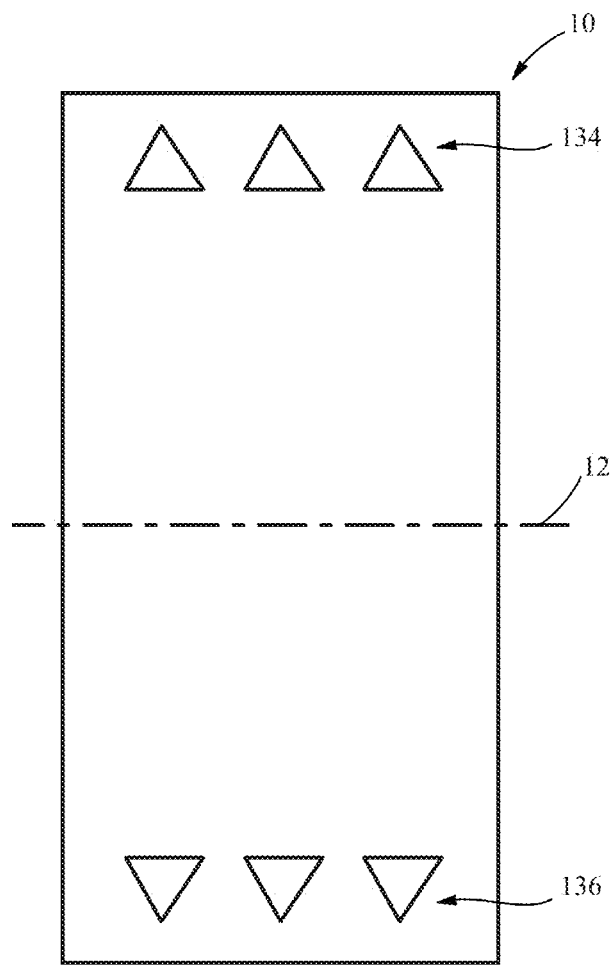
Figure 29:
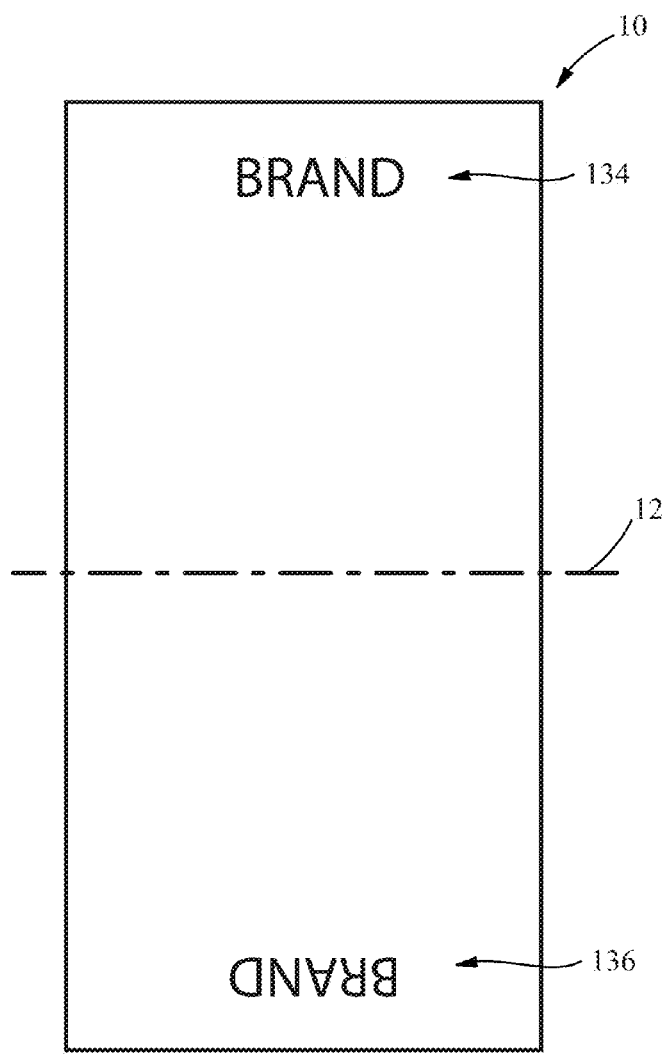

FIGS. 27-29 are schematic illustrations of absorbent articles 10 with graphics and/or indicia 134, 136 (hereafter "graphics"), with their garment-facing surfaces facing the viewer. The graphics 134 may be on a first side of the central lateral axis 12 and viewable from the garment-facing surface and the graphics 136 may be on a second side of the central lateral axis 12 and viewable from the garment-facing surface of the absorbent article 10. The graphics 134 and/or 136 may or may not cross the central longitudinal axis of the absorbent article 10. The graphics 134 and/or 136 may be a single graphic or multiple graphics that form a single image, multiple images, single patterns, or multiple patterns. The graphics 134 may be a mirror image of the graphics 136 (or may be the same or substantially the same), relative to the central lateral axis 12, to indicate reversibility of the absorbent article to a caregiver or wearer. In other instances, the graphics 134 may not be a mirror image of the graphics 136, relative to the central lateral axis 12. Referring to FIG. 29, the graphics 134 and/or 136 may be at least partially comprised of brand names, characters, and/or logos. The graphics 134 and/or 136 may be printed on, positioned on, and/or applied to the backsheet 38 and/or the outer cover nonwoven material 58, for example. If the graphics 134 and 136 are on the backsheet 38, the outer cover nonwoven material 58 may have an opacity such that the graphics 134 and 136 are viewable therethrough. The graphics 134 and 136 may be on a garment-facing side of the backsheet 38 and/or the wearer-facing side of the backsheet 38. The graphics 134 may also be printed on, or otherwise applied to, a landing zone in the front waist region 16. Likewise, the graphics 136 may be printed on, or otherwise applied to, a landing zone in the back waist region 18. By providing two landing zones, the caregiver is able to recognize that the absorbent article 10 is reversible. The landing zones may be a separate material joined to the outer cover nonwoven material 58 or may be formed by portions of the outer cover nonwoven material 58.

By having graphics 134 and 136 that are mirror images of each other, relative to the central lateral axis 12, the absorbent article 10 may be reversible. Stated another way, a baby's (or wearer's) back waist region may be positioned adjacent to graphics 134 or 136 depending on how the absorbent article 10 is donned on the baby. If the absorbent article 10 is meant to be reversible, the absorbent material 42 within the absorbent core 40, in some instances, may be uniform and homogeneous. The absorbent core 40 may also be longitudinally centered in the absorbent article to aid in reversibility of the absorbent article. By providing graphics that mirror each other on opposite sides of the central lateral axis 12, a caregiver will quickly recognize that the absorbent article is reversible. Further, the graphics may indicate where fasteners (e.g., 110, 112) may be attached (e.g., landing zone) on the garment-facing surface to provide a caregiver with a guide as to proper application of the fasteners and, thereby, a proper application of the absorbent article 10.

Referring to FIGS. 8 and 30-34, one or more inserts 140 may be provided for use with the absorbent article 10. The one or more inserts 140 may be packaged together with the absorbent article 10 or packaged and sold separately. One or more inserts 140 and one or more absorbent articles 10 may be in a kit. The one or more inserts 140 may be positioned within the absorbent article 10 after the absorbent article 10 is donned on the wearer or before the absorbent article 10 is donned on the wearer. The inserts 140 essentially provide an additional absorbent containment element that may be used prior to soiling the absorbent article 10 or after soiling of the absorbent article 10. The inserts 140 may be advantageous in that the baby or wearer may not need to be fully changed and, thereby, moved or handled less, compared to if only the absorbent article 10 was used. Multiple inserts may be used at one time, so that once soiled the most wearer-facing insert may be removed. In some instances, the inserts 140 may be fastening or joined to the wearer-facing surface of the absorbent article 10 or to a wearer-facing surface of another insert using any suitable joining techniques. In other instances, the inserts 140 may merely be placed on the wearer-facing surface of the absorbent article 10 or the wearer-facing surface without some separate attachment or joining mechanism. In these instances, the inserts 140 may remain in place by friction or merely by weight of the baby. In some instances, at least portion of the inserts may have low coefficients of friction to allow them to slide over a portion of a wearer-facing surface of the absorbent article 10, when being inserted into the absorbent article while it is on a wearer. The inserts are helpful as full absorbent article changes may be reduced, thereby leading to less stress on (i.e., less movement of) a baby or premature baby.

Figure 30:
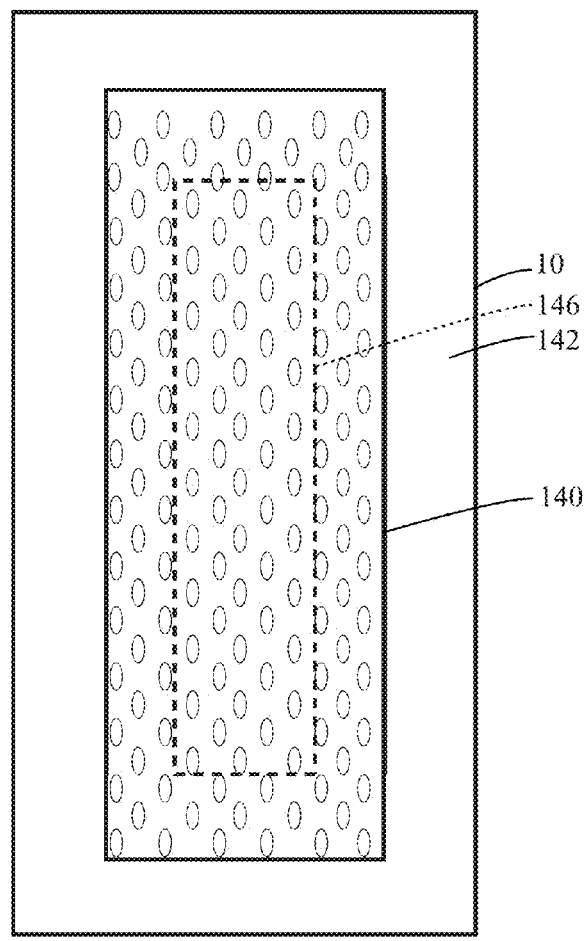
FIG. 30 is a plan view of an example insert positioned on a wearer-facing surface of an absorbent article.
Figure 31:
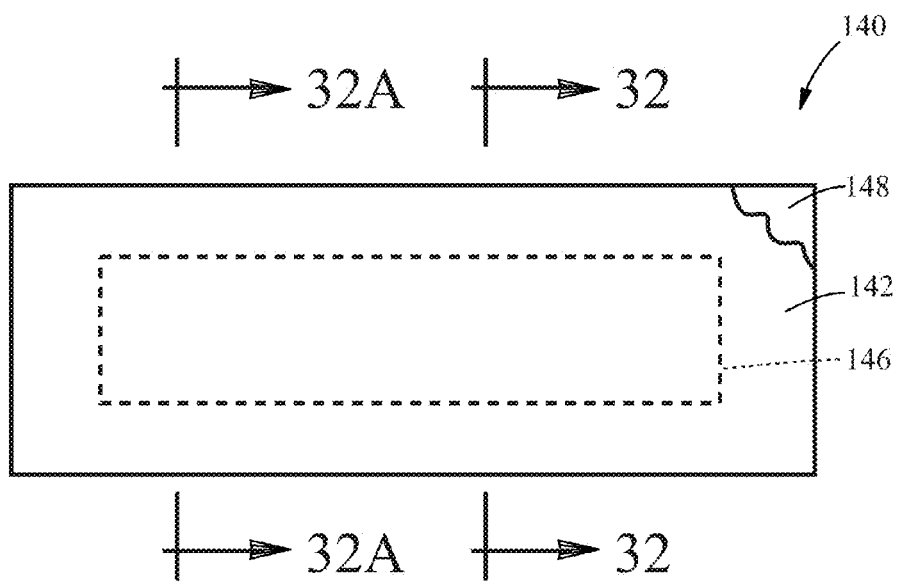
FIG. 31 is a plan view of an example insert for use with an absorbent article.
Figure 32:
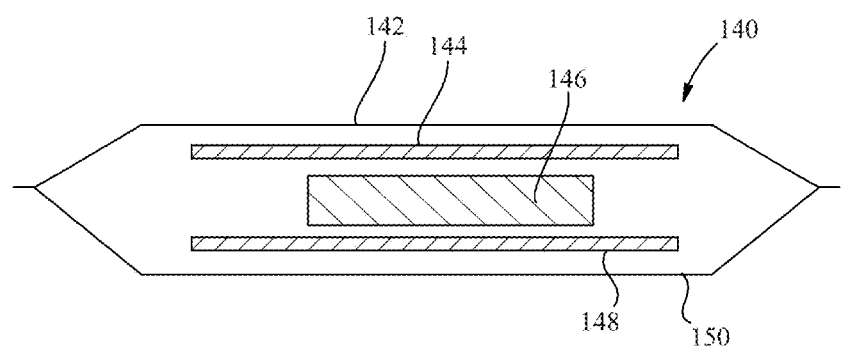
FIG. 32 is a cross-sectional example illustration of the insert, taken about line 32-32 of FIG. 31.

FIG. 30 is a plan view of the insert 140 positioned on a wearer-facing surface of an absorbent article 10 of the present disclosure. FIG. 31 is a plan view of the insert. FIG. 32 is a cross-sectional illustration of the insert 140 of FIG. 31, taken about line 32-32. FIG. 33 is a plan view of another insert 140'. FIG. 34 is a plan view of another insert 140".

The inserts 140 may comprise a topsheet 142, an optional acquisition material and/or distribution material 144, an absorbent core 146, a backsheet 148, and optionally an outer cover nonwoven material 150. The topsheet 142 may be formed of one or more nonwoven materials, one or more films, or a laminate formed of one or more nonwoven materials and one or more films. The topsheet 142 may comprise a liquid permeable material or apertures 152 defined in the topsheet 142 may make the topsheet 142 liquid permeable or more liquid permeable. The topsheet 142 may also comprise three-dimensional features, embossments, bond patterns, lotions, and/or surfactants, for example. The acquisition material and/or distribution material 144 may be formed of nonwoven materials, foams, or other suitable materials. The acquisition material and/or distribution material 144 is only illustrated in FIG. 32, since it is an optional feature. Optionally, a layer of cross-linked cellulosic fibers may also be present intermediate the topsheet 142 and the acquisition material and/or distribution material 144. The absorbent core 146 may comprise an absorbent material. The absorbent material may comprise airfelt and superabsorbent polymers, mostly or only airfelt, or mostly or only superabsorbent polymers. The absorbent core 146 may have areas that are free of the absorbent material (e.g., channels that are free of the absorbent material) or may have areas where the absorbent material is densified (e.g., channels that are formed by densified areas in the absorbent material). The backsheet 148 may be liquid impermeable, and may or may not be air permeable (or "breathable"). In some instances, the backsheet 148 may not be provided and bodily exudates that are not absorbed by the absorbent core 146 may pass through the insert 140 and into the absorbent articles 10. The outer cover nonwoven material 150 may or may not be provided and may be formed of a nonwoven material, for example.

Figure 32A:
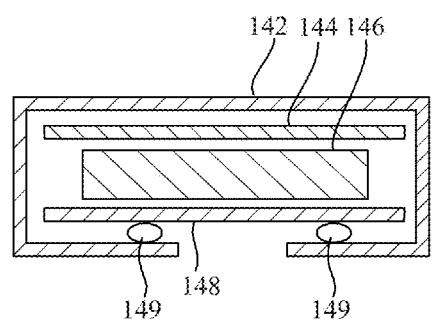
FIG. 32A is another cross-sectional example illustration of the insert, taken about line 32A-32A of FIG. 31.

Referring to FIG. 32A, in some instances, the insert 140 may have the cross section illustrated when taken about line 32A-32A of FIG. 31. In such an instance, the topsheet 142 may form a C-wrap around end regions of the backsheet 148 and be joined to the backsheet 148 using adhesive bonds 149, or other types of joining. In such an instance, a portion of the backsheet 148 may rest on the topsheet 36 of the absorbent article 10. Stated another way, a portion of the backsheet 148 may form a garment-facing surface of the insert. An optional acquisition material and/or distribution material 144 may be provided. The insert of FIG. 32A may, in some instances, have an outer cover nonwoven material as well.

Referring to FIG. 33, an insert 140' is illustrated. This example insert 140' has a grasp tab 154 on one end and a cut out 156 on the other end. The grasp tab 154 may be used by a caregiver to easily grasp and remove the insert 140'. The grasp tab 154, in an example, may be formed only of a backsheet material, or other liquid impermeable material, so that bodily exudates cannot wick to the grasp tab 154. In other instances, the grasp tab 154 may be formed of a portion of the topsheet 142, a portion of the backsheet 148, and/or a portion of the outer cover nonwoven material 150. By providing the grasp tab 154 on one end and the cut out 156 on the other end, a material savings may be achieved when the inserts are manufactured in strip of a plurality of the inserts 140'. Any of the inserts described herein may be manufactured in a strip of a plurality of the inserts and may be packaged as a roll of inserts, for example. Lines of weakness 158 may be formed intermediate the various inserts. In such an instance, a roll of a plurality of inserts may be provided to a caregiver or nurse and the caregiver or nurse can then tear off any suitable number of inserts for use on a particular wearer. The inserts may also be packaged in stacks, for example, or in other forms.

Referring to FIG. 34, the insert 140" is illustrated. The example insert 140" may have a grasp tab 154 on both ends to allow for easier caregiver or nurse placement and removal of the inserts 140".

In some instances, the various inserts may comprise stiffening members or stiffened portions (e.g., foams, densified regions) to aid in application of the inserts into a donned absorbent article 10.

In some instances, it may be desirable for the absorbent articles to be free of fragrances, perfumes, and/or lotions. In other instances, one or more components of the absorbent articles, such as the topsheet, for example, may be free of fragrances, perfumes, and/or lotions.

Figure 35:
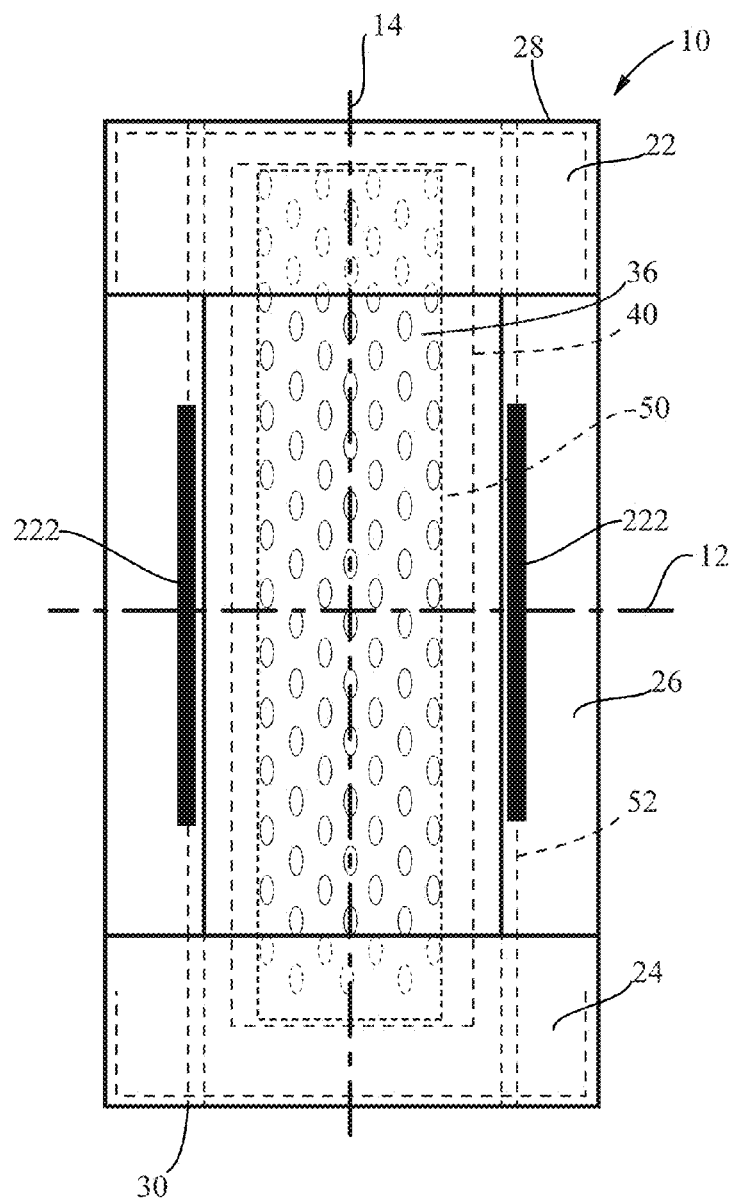
FIG. 35 is a plan view of an example absorbent article, wearer-facing surface facing the viewer.
Figure 36:
FIG. 36 is a perspective side view photograph of an example absorbent article.
Figure 37:
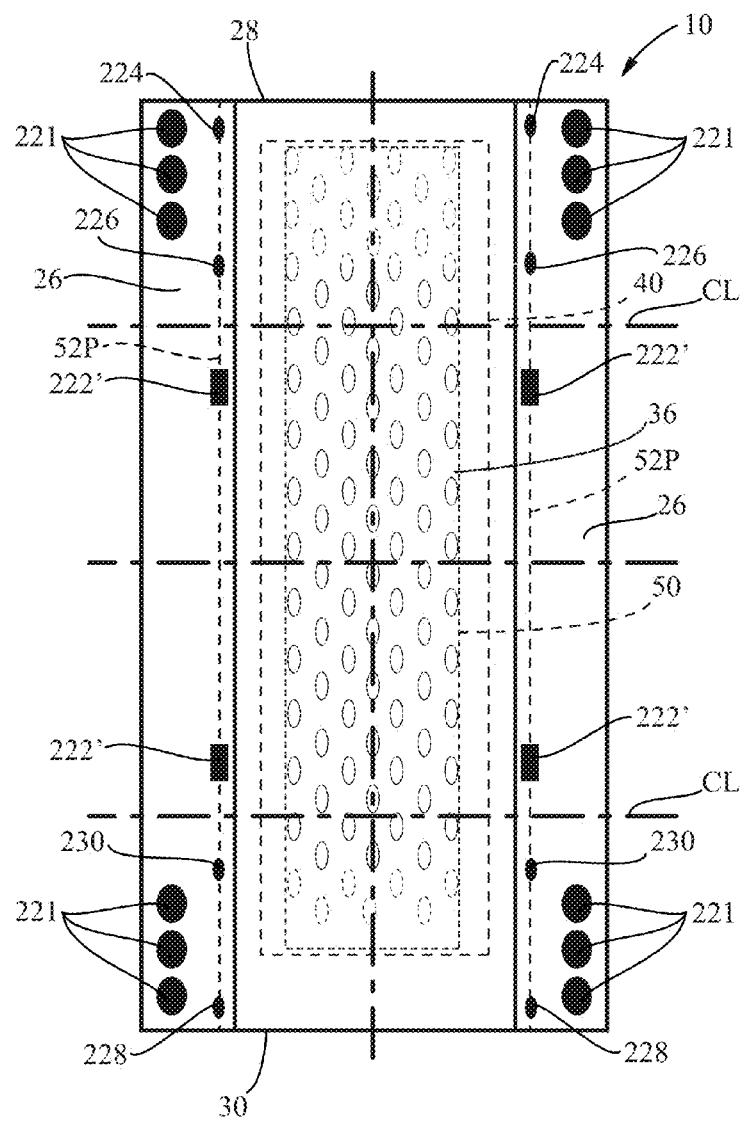
FIG. 37 is a plan view of an example absorbent article, wearer-facing surface facing the viewer.

Referring to FIG. 35, the elastics 52 may extend the full longitudinal direction, substantially the full longitudinal direction, or only part of the full longitudinal direction of the absorbent article 10. In certain instances though, the elastics 52 may only be joined to the cuffs 26 in a joined area 222. The elastics 52 may not extend the full longitudinal direction of the absorbent article 10 after the absorbent article is separated from other absorbent articles at the first end edge 28 and at the second end edge 30. In this instance, the elastics 52 may "snap back" toward the joined area 222. Portions of the elastics 52 outside of the joined area 222 may be free of joinder to the cuffs 26, thereby not applying elastic forces to areas of the cuffs 26 outside of the joined area 222. The joined area 222 may be centrally located on the elastics 52 in the longitudinal direction (i.e., a direction about the longitudinal axis 20). Stated another way, the joined area 222 may exhibit symmetry with respect to the lateral axis 12. In other cases, the joined area 222 may not exhibit symmetry with respect to the lateral axis 12 or may not even cross the lateral axis 12. In this instance, the joined area 222 may be fully positioned on a first side of the lateral axis 12 or may be fully positioned on a second side of the lateral axis 12. More than one joined area 222 may exist for a single cuff 26. In a single elastic 52, one joined area may be on the first side of the lateral axis 12 and a second joined area may be on a second side of the lateral axis 12. The joined areas 222 may have a length extending in a direction generally parallel to the longitudinal axis 14 of about 0.25 inches to about 10 inches, about 0.5 inches to about 7 inches, about 1 inch to about 6 inches, about 1 inch to about 5 inches, or about 1 inch to about 4 inches, specifically reciting all 0.1 inch increments with the specified ranges and all ranges formed therein or thereby. The certain longitudinal length of the joined areas 222 in a particular absorbent article 10 may depend on the size of the absorbent article 10 and/or the intended use of the absorbent article 10. The joined area 222 may comprise one or more adhesives and/or one or more mechanical, ultrasonic, and/or thermal bonds, for example, to join the elastics 52 in the joined area 222 to the cuffs 26. The joined areas 222 are illustrated as a rectangular block for illustration purposes only, and other suitable shapes are within the scope of the present disclosure. The elastics 52 may be under a pre-strain when joined to the cuffs 26 to activate the joined areas 222 when the pre-strain is released. In some instances, the elastics 52 may only extend longitudinally through the joined area 222 and may be pre-strained. The cuffs 26 may be formed of one or more materials or nonwoven materials. If only one material is used, that material may be folded over itself to enclose the elastics 52. If two materials are used, the materials may sandwich the elastics therebetween. The joined area 222 may be two or more discrete bonds 222' with pre-strained elastics 52P therebetween as illustrated in FIG. 37. The elastics 53, if provided, may have the same or different features as the elastics 52 described in this paragraph. In other instances, only the elastics 53 may have the features described in this paragraph with respect to the elastics 52. By providing elastics 52 and/or 53 with one or more joined areas 222, the absorbent pad may form a U-like shape by bringing the first end edge 28 towards the second end edge 30. This may provide better bodily exudate containment. An example absorbent article having this U-like shape is illustrated in FIG. 36.

In other instances, the joined areas 222 may not be provided and the cuffs may comprise a first nonwoven substrate or a first substrate and a second nonwoven substrate or a second substrate. The first and second nonwoven substrates may be joined to each other at different longitudinal pre-strain forces. As such, when these pre-strain forces are released, the cuff may contract and form a structure like the top absorbent article of FIG. 36. One pre-strain force in one of the first and second substrates may be negligible or may be zero.

Figure 38:
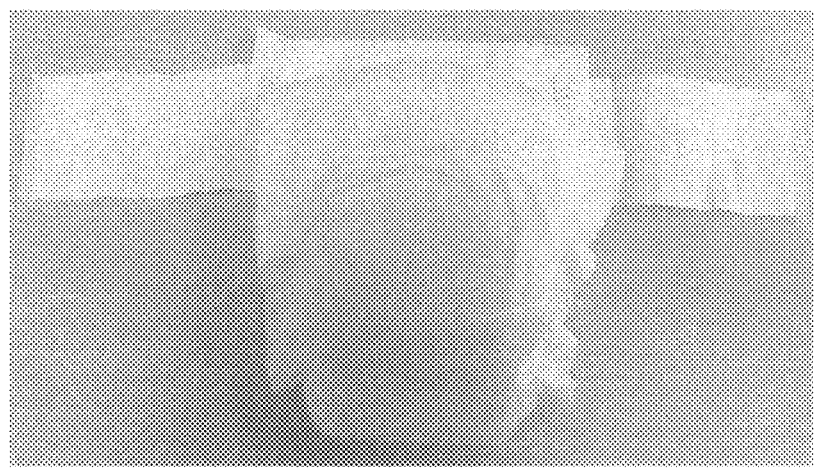
FIG. 38 is a front perspective view of an example absorbent article.
Figure 39:
FIG. 39 is a side perspective view of an example absorbent article.
Figure 40:
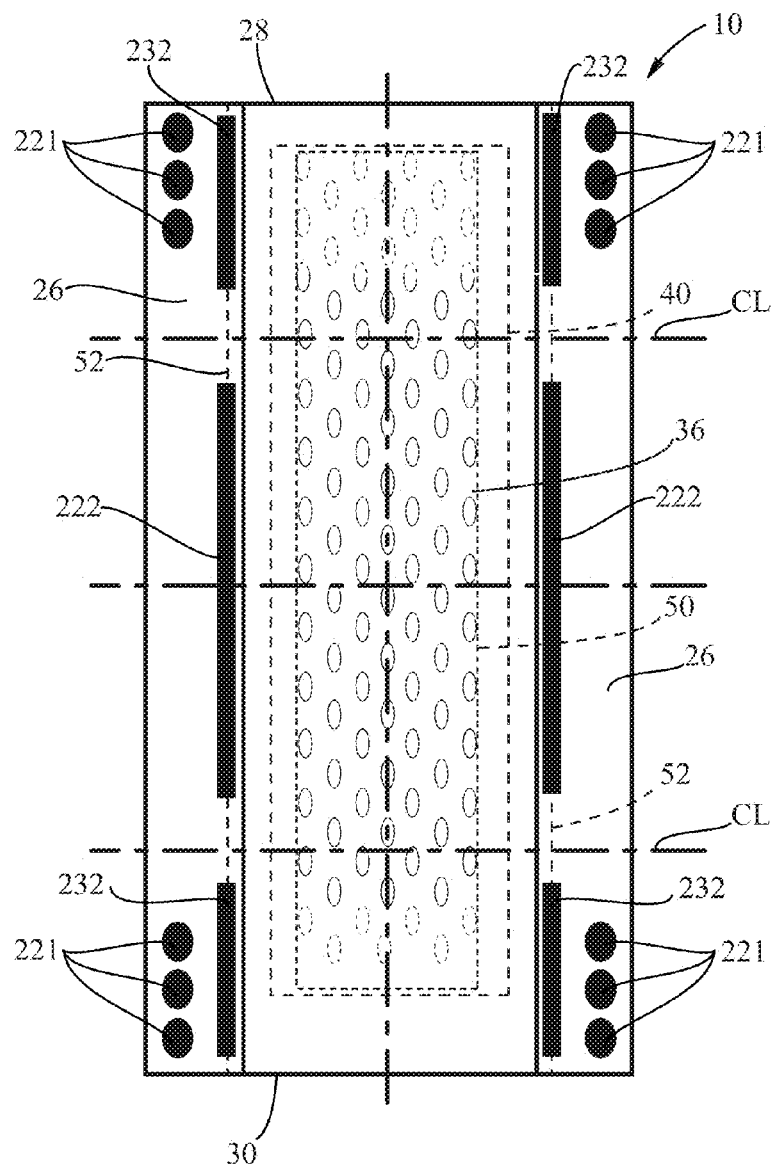
FIG. 40 is a plan view of an example absorbent article, wearer-facing surface facing the viewer.

Referring to FIG. 37, an absorbent article 10 may have cuffs 26 with a certain elastic configuration. The elastics 52 and/or 53 may or may not have the joined areas 222, 222' discussed above. The elastics 52 may each have a first bond 224 proximate to the first end edge 28 and a second bond 226 positioned more distal from the first end edge 28 than the first bond 224. The elastics 52 may also each have a third bond 228 proximate to the second end edge 30 and a fourth bond 130 positioned more distal from the second end edge 30 than the third bond 228. The elastics 52 may be cut (example cut lines "CL" illustrated in dash in FIG. 37) intermediate the second bond 226 and joined area 222 (or 222') or, if the joined area 222 is not provided, intermediate the second bond 226 and the fourth bond 230. If the joined area 222 is provided, the elastics 52 may also be cut intermediate the fourth bond 230 and the joined area 222. The bonds 224 and 226, owing to contraction of the elastic 52 therebetween, may cause the first end edge 28 to curl or fold over a portion of the wearer-facing surface proximate to the first end edge 28. The bonds 228 and 230, owing to the contraction of the elastic 52 therebetween, may cause the second end edge 30 to curl or fold over a portion of the wearer-facing surface proximate to the second end edge 30. These curled or folded over portions may help contain bodily exudates on the absorbent article 10 so that they may be absorbed by the absorbent core 40 and so that clothing around the absorbent article 10 is not soiled. FIG. 38 is a perspective front view of a curled or folded over portion of an absorbent article in the front waist region. FIG. 39 is a perspective view of the curled or folded over portion of an absorbent article in the front waist region. The back waist region may also have the curling or folded over features in the example absorbent articles of FIGS. 38 and 39. These features may be used with or without the various wetness guards 22, 24 disclosed herein. In other instances, these curled or folded over portions may be used to create the wetness guards 22, 24 when they are curled or folded over. When used as wetness guards, the curled or folded over portions may be tacked, bonded, and/or glued to the wearer-facing surface to hold them in place. The elastics 53 of the cuffs 27, if provided, may have the similar or the same features as the elastics 52 of the cuffs 26 described in this paragraph. The bonds 224, 226, 228, and 230 may comprise adhesive bonds, mechanical bonds, ultra-sonic bonds, and/or thermal bonds, for example. One or more tack down bonds 221 may also be present on the absorbent article 10. The tack down bonds 221 may be used to join the cuffs 26 to the topsheet or to other portions of the absorbent article 10. Referring to FIG. 40, instead of providing the first, second, third, and fourth bonds 224, 226, 228, and 230, a continuous bond 232 may be provided in at least one end region of the elastics 52. The continuous bond 232 may function like the first, second, third, and fourth bonds 224, 226, 228, and 230 described above and may result in curled or folded portions illustrated in FIGS. 38 and 39. The continuous bonds 232 may comprise adhesive bonds, mechanical bonds, ultra-sonic bonds, and/or mechanical bonds, for example. Continuous bonds may also be provided on the elastics 53 of the cuffs 27, if provided. The elastics may be pre-strained before the continuous bond is applied such that elastic contraction within the continuous bonds may cause the end portions to curl or fold over.

Figure 41:
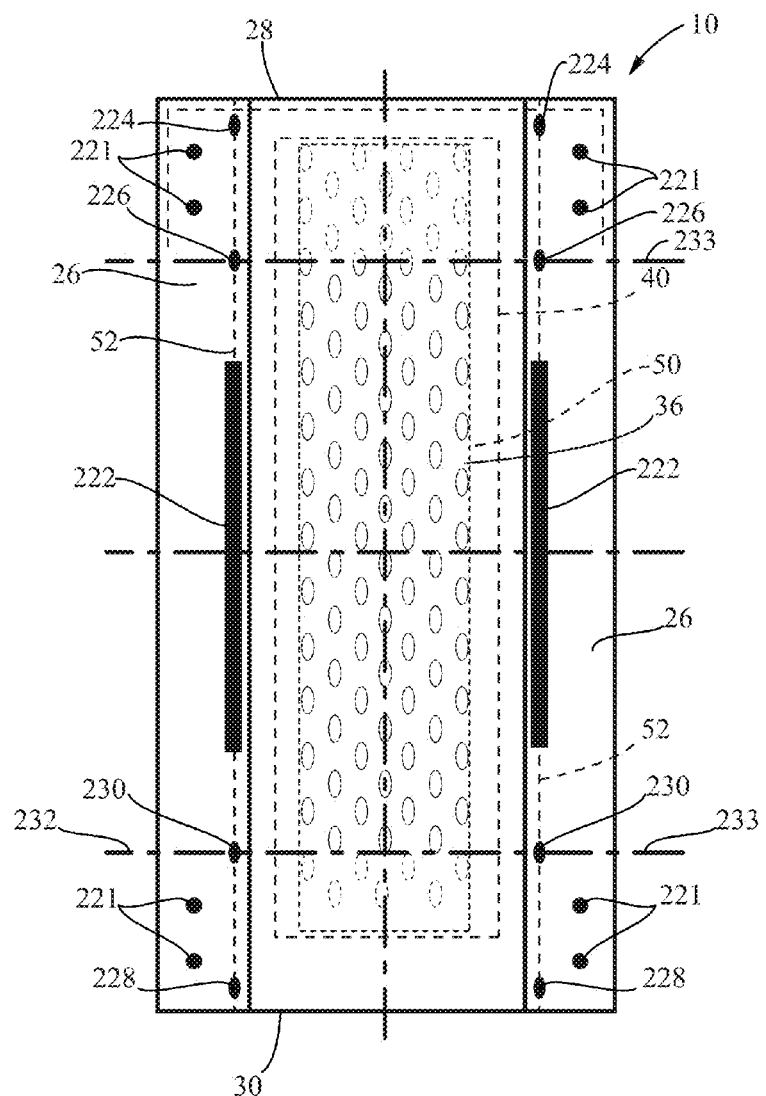
FIG. 41 is a plan view of an example absorbent article, wearer-facing surface facing the viewer.

Referring to FIG. 41, portions of the absorbent core 40, the absorbent material 42 within the absorbent core 40, and/or other layers of the absorbent articles may comprise one or more fold lines 233 to allow easier folding of portions of the absorbent articles 10. The fold lines 233 may be areas with reduced or no absorbent material 42 or embossed areas, for example. The fold lines may be at any suitable locations within the absorbent core 40 and/or the absorbent article 10. The fold lines may be helpful to a caregiver or nurse when situating the absorbent pad 10 at least partially around a baby, for example.

Methods for producing cuffs of the absorbent articles are also disclosed. The cuffs may be made online or by hand. In an online context, a first nonwoven web or a first web may be advanced (e.g., on a conveyor) in a machine direction. One or more elastics may be applied in a pre-strained condition to the first nonwoven web. The pre-strained elastic may have the same machine direction length as the first nonwoven web. The pre-strained elastic may be joined to the first nonwoven web in a plurality of joined areas 222 (e.g., one or more joined areas per discrete cuff length). In some instances, the pre-strained elastic may only be joined to the first nonwoven web in the joined areas 222. The joining may use adhesives or bonds, as discussed herein. The remainder of the elastic outside of the joined areas 222 may be free of joinder to the first nonwoven web. The first nonwoven web may then be folded over itself to enclose the elastic. In other instances, a second nonwoven web or second web may be positioned over the first nonwoven web and may be joined to the first nonwoven web to enclose the elastic. The second nonwoven web may also be joined to the elastic in the joined areas 222. The formed web of cuffs may then be cut to suitable discrete lengths. When the web of cuffs is cut to suitable discrete lengths, the elastic in each cuff may "snap back" towards the joined areas 222, leaving the elastic only pre-strained in the joined area, with the remainder of the elastic being non-pre-strained and not attached to the first and/or second nonwoven discrete webs. The cuffs may then be attached to an absorbent article. Once the cuffs are attached to an absorbent article, the structure of FIG. 36 may be created. In some instances, the first nonwoven web may first be joined to a moving web comprising a topsheet, a backsheet, and an absorbent core positioned at least partially therebetween, among other components (e.g., an acquisition layer positioned intermediate the topsheet and the absorbent core). In this instance, the cuffs and the moving web may be cut into discrete absorbent articles at the same time.

In addition to being joined to the first and/or second nonwoven webs in the joined areas 222, the elastics may also be joined to the first and/or second nonwoven webs at bonds (e.g., bonds 224, 226, 228, and 230 or continuous bonds 232). These features may apply in a single web cuff that is folded over itself or to a two web cuff. Also, the elastics may only be joined to the first and/or second nonwoven webs at the bonds and not in the joined areas 222. In any event, if the elastics are joined to the bonds (e.g., 224 and 226), portions of the elastics intermediate the bonds will remain pre-strained after the elastics are cut intermediate bond pairs (e.g., "CL" of FIG. 37) and after the cuffs are cut into suitable discrete lengths. This may cause the pre-strained elastic portions intermediate the bonds (e.g., 224 and 226), to contract upon release of the pre-strain force and cause the curling or folding of longitudinal end portions as illustrated in FIGS. 38 and 39.

Figure 42:
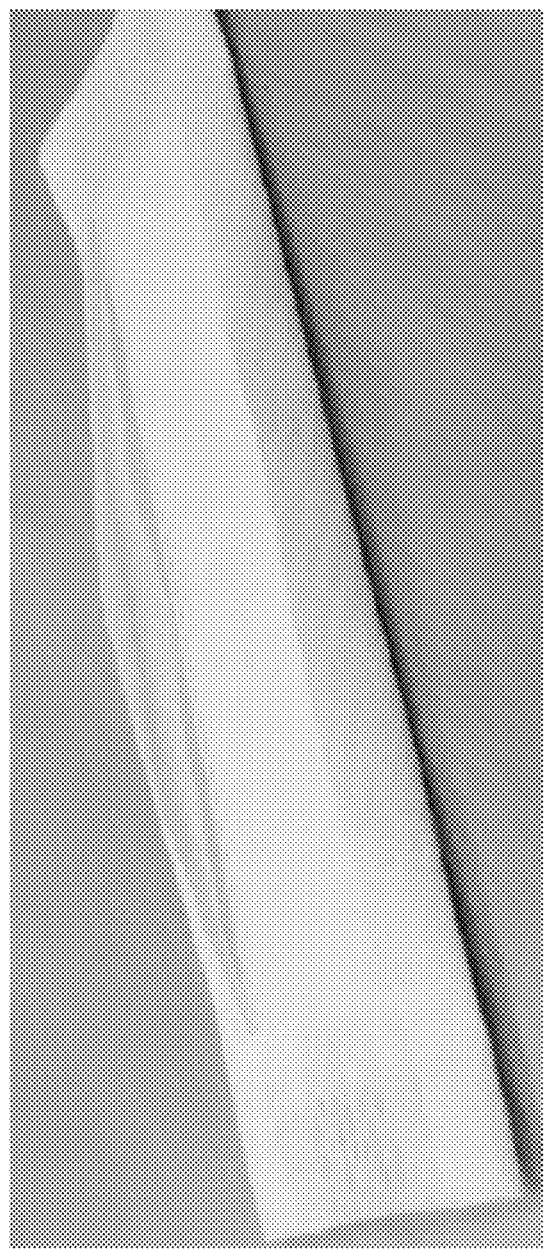
FIG. 42 is a perspective view photograph of an absorbent article with folded over cuffs, wearer-facing surface facing away from the surface on which the absorbent article is resting.
Figure 43:
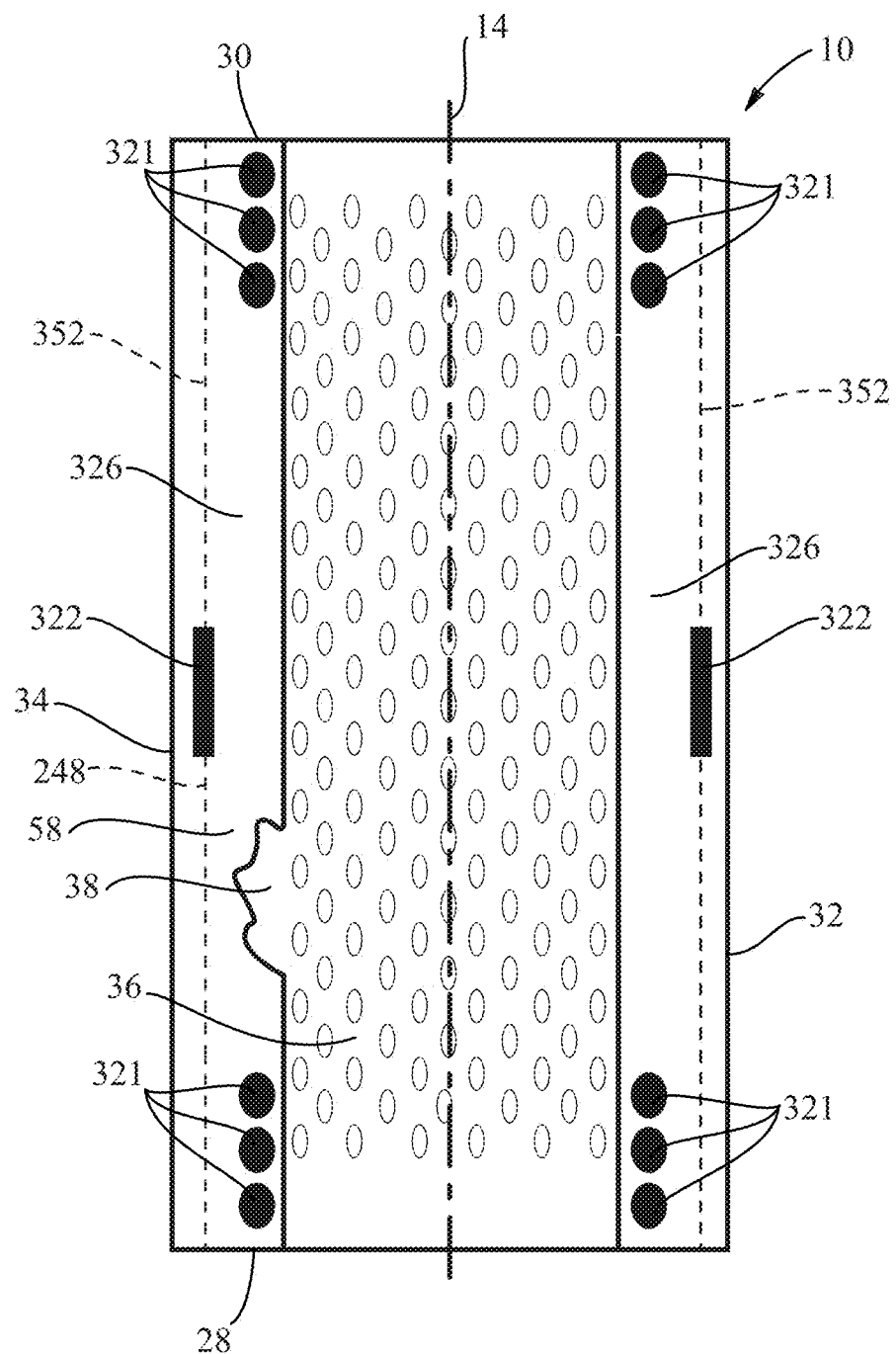
FIG. 43 is a plan view of an absorbent article with folded over cuffs.
Figure 44:
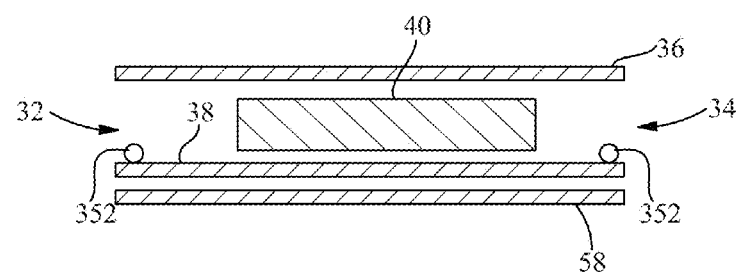
FIG. 44 is an example cross-sectional view of the absorbent article prior to the cuffs being folded toward the longitudinal axis.
Figure 45:
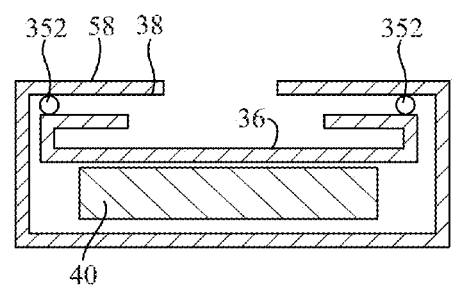
FIG. 45 is an example end view of the absorbent article of FIG. 43 before any tack down bonds are applied.

In some instances, discrete cuffs, like the pairs of cuffs 26 and 27 may not be provided in an absorbent article. Instead, referring to FIGS. 42-45, a pair of cuffs 326 may be integrally formed in the absorbent article 10 by folding the first and second side edges 32 and 34 inwardly toward the longitudinal axis 14. FIG. 42 is a perspective view photograph of an absorbent article with folded over cuffs. FIG. 43 is a plan view of an absorbent article 10 with folded over cuffs 326. FIG. 44 is an example cross-sectional view of the absorbent article 10 prior to the cuffs 326 being folded toward the longitudinal axis 14. FIG. 45 is an example end view of the absorbent article 10 of FIG. 43 before any tack down bonds are applied.

Referring to FIGS. 43-45, the structure of the absorbent article 10 is illustrated. The absorbent article 10 comprises a topsheet 36, an absorbent core 40, a backsheet 38, and an outer cover nonwoven material 58. The absorbent core 40 is disposed at least partially between the topsheet 36 and the backsheet 38. Elastics 352 may also be positioned intermediate the topsheet 36 and the backsheet 38 or may be positioned intermediate the backsheet 38 and the outer cover nonwoven material 58. Portions of the topsheet 36, the backsheet 38, and the outer cover nonwoven material 58 may be folded towards the longitudinal axis 14 to create a structure like that illustrated in FIGS. 43 and 45. The elastics 352 may only be joined to the cuff 326 in a joined area 322, much like joined area 222. The joined area 322 may comprise an adhesive that joins the elastics 352 to the topsheet 36 and/or backsheet 38 (or to the backsheet 38 and/or the outer cover nonwoven material 58). One or more tack down bonds 321 (similar to tack down bonds 221 described herein) may also be present on the absorbent article 10 proximate to the first end edge 28 and the second end edge 30. The tack down bonds 321 may be used to hold the ends of the cuffs 326 in the folded over configuration. In some instances, the elastics 352 may not be provided and the cuffs 326 may "stand" because of the tack down bonds 321. Any suitable number of tack down bonds 321 may be provided.

The tack down bonds 321 in combination with the joined area 322 of the elastics 352 may cause the cuffs 326 to "stand" more than without the elastics 352 and the joined area 322 as illustrated in FIG. 42. In some instances, the elastics 352 may be joined to the topsheet 36 and/or backsheet 38 (or to the backsheet 38 and/or the outer cover nonwoven material 58) along their full length or along most of their length. Other features, such as the wetness guards 22, 24, for example, of the absorbent articles 10 described herein may also be used with the absorbent article of FIGS. 42-45. One or more acquisition materials and/or distribution materials may also be provided at least partially intermediate the topsheet 36 and the absorbent core 40, similar to acquisition material 50 and distribution material 51 described herein.

Figure 46:
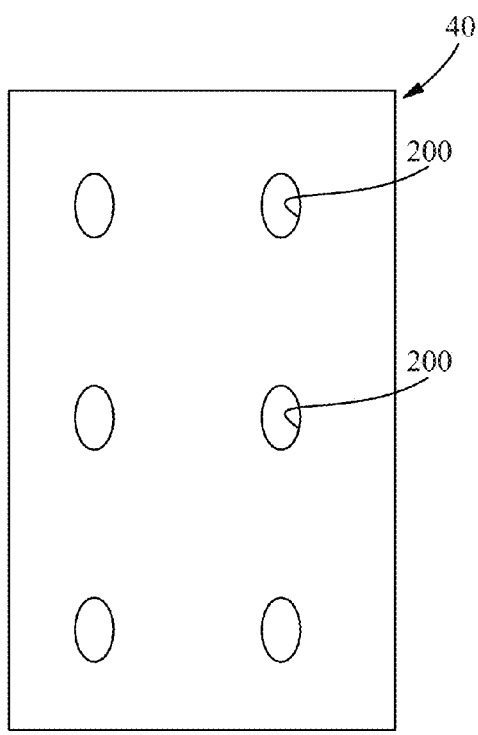
FIG. 46 is an example plan view of an absorbent core of an absorbent article.

Referring to FIG. 46, an absorbent core 40 of any of the absorbent articles 10 disclosed herein may have apertures 200 defined therein. Any suitable number of apertures may be provided and the apertures 200 may have any suitable shape, such as round or ovate, for example. The apertures 200 may also have any suitable size. The apertures 200 may all be the same in size and/or shape or may be different in size and/or shape. The apertures 200 may be dispersed uniformly or non-uniformly in the absorbent core 40. The apertures 200 may make the absorbent core more flexible and allow the absorbent core to fold or flex easier. The absorbent core may be shaped as discussed herein.

Figure 47:
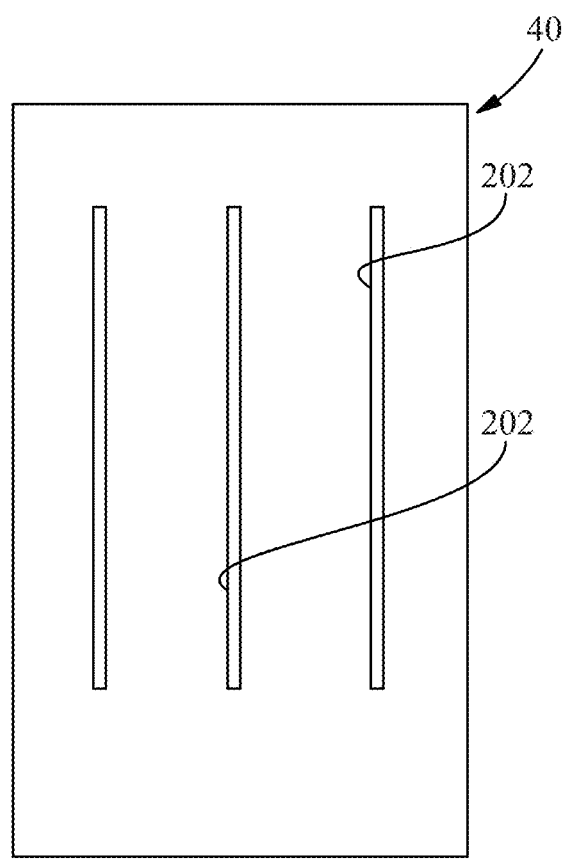
FIG. 47 is an example plan view of an absorbent core of an absorbent article.

Referring to FIG. 47, an absorbent core 40 of any of the absorbent articles 10 disclosed herein may have slots 202 defined therein. Any suitable number of slots 202 may be provided and the slots 202. The slots 202 may all be the same in size and/or shape or may be different in size and/or shape. The slots 202 may be linear or non-linear, continuous or discontinuous. The slots 202 may extend in any suitable direction. The slots 202 may have any suitable width. In some instances, the slots 202 may not have material removed in their creation, but may only be cut lines in the absorbent core 36. The slots 202 may be distributed uniformly or non-uniformly in the absorbent core 40. The slots 202 may make the absorbent core 40 more flexible and allow the absorbent core 40 to fold or flex easier. The absorbent core may be shaped as discussed herein.

Test Methods

For all test methods, condition the samples at 23° C.±2 C° and 50%±2% relative humidity for 2 hours prior to testing.

Crotch Compression Force Measurement Test

Figure 48:
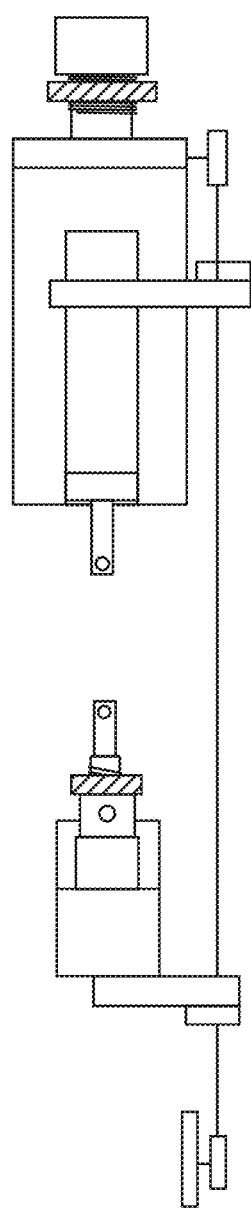
FIG. 48 is a top view of an instrument used in the Crotch Compression Force Measurement Test.
Figure 49:
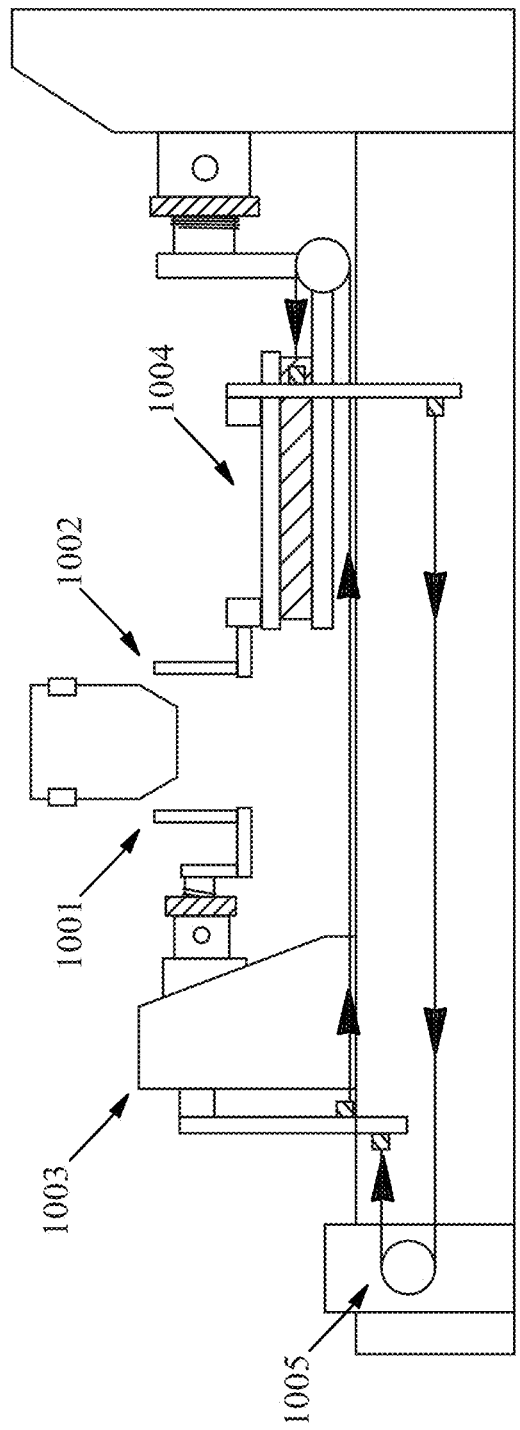
FIG. 49 is a side view the instrument used in the Crotch Compression Force measurement Test.

The Crotch Compression Force Measurement Test is measured using a horizontally oriented constant rate of extension tensile tester (FIGS. 48 and 49) with a computer interface (a suitable instrument is a horizontally oriented MTS Criterion 42 interfaced with a computer running TestWorks 4 software, as available from MTS Systems Corp., Eden Prairie, Minn.) using an S-beam type load cell, with moment or off-axis side load cancelling capabilities, for which the forces measured are within 10% and 90% of the limit of the cell. Two vertically oriented cylindrical posts (1001 and 1002), each with a diameter of 7.0 mm, are utilized to compress the sample. One post is affixed to the moveable crosshead (1003), and the other is affixed to a moveable sled (1004) as part of the stationary test fixture. The absorbent article sample is suspended between the vertical compression posts. The posts are then simultaneously brought together, compressing the crotch region of the sample, simulating the compression at the crotch region of an absorbent article from the legs of the wearer during normal use. During the experiment the instrument collects force and distance data. All testing is performed in a conditioned room maintained at about 23° C.±2 C and about 50%±2% relative humidity.

Accurately align the vertical compression posts so that they are vertically parallel to each other and are horizontally aligned along the central axis of the instrument's moveable fixture travel path. One post is affixed to the moveable crosshead, and the other is affixed to a moveable sled on the stationary fixture. By way of a pulley and cable system (1005), as the crosshead travels toward the stationary fixture it causes the sled affixed to the stationary fixture to simultaneously travel at the same rate toward the crosshead. This allows the two compression posts to travel in a linear path toward each other during the experiment.

Remove the individual samples from any outer packaging, and allow them to precondition at about 23° C.±2 C.° and about 50%±2% relative humidity for 2 hours prior to testing. Open the sample and secure the middle 50 mm of the front and back waist edges to either side of a 25.4 mm wide support bar, so that the crotch region of the sample is suspended in a "U" shape between the compression posts. The sample is centered between the compression posts and aligned so that the crotch region will be laterally compressed during the experiment. Separate the compression posts so that the interior gap between them is wide enough to not initially touch either side of the sample prior to testing. The suspended sample is lowered into position for testing, so that the bottom of the crotch region is 15 mm below the top of the compression posts.

Program the tensile tester to perform a compression test, collecting force and extension data at an acquisition rate of 50 Hz as the crosshead travels at a rate of 120 mm/min, which equates to the compression posts moving toward each other at a rate of 240 mm/min, until the gap between the compression posts is equal to 20 mm. Zero the load cell; start the tensile tester and the data acquisition. Program the software to record the force when the interior gap between the compression posts is equal to 20 mm to the nearest 0.001 N. Repeat this procedure for 10 substantially similar samples. Average together the 10 individual Crotch Compression Force measurements and report the value nearest 0.001 N.

Opacity Test

Separate the outer cover nonwoven material and backsheet from the absorbent article samples using cryogenic spray.

Opacity by contrast ratio measurements are made using a 0°/45° spectrophotometer suitable for making standard CIE L*a*b* color measurements (e.g., Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2C.° and 50%±2% relative humidity.

Calibrate the instrument per the vender instructions using the standard black and white tiles provided by the vendor. Set the spectrophotometer to use the CIE XYZ color space, with a D65 standard illumination and 10° observer. Using cryogenic spray and scissors carefully excise the specimen from the article for testing. The region of interest is selected from the crotch region near the longitudinal centerline of the chassis excluding significant wrinkles, creases, or wetness indicators. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing, then multiplying the ratio by 100. Record the opacity value to the nearest 0.01%. Calculate opacity for the 10 replicates and report the average opacity to the nearest 0.01%.

Folded Crotch Width Test

The Folded Crotch Width (W) (see FIG. 1) is measured by folding an absorbent article sample so that the front and back waist edges are aligned, and so that corresponding lateral edges are aligned with each other. Using a calibrated ruler certified by NIST, measure and record the lateral width of the outer surface of the sample along the fold to the nearest 0.1 mm. Repeat this procedure for 10 substantially similar absorbent articles samples. Average together the 10 individual Folded Crotch Width (W) measurements and report the value nearest 0.1 mm.

Folded Crotch Angle Test

The Folded Crotch Angle (A) (see FIG. 1) is measured by folding an absorbent article sample so that the front and back waist edges are aligned, and so that corresponding lateral edges are aligned with each other. Using a calibrated protractor certified by NIST measure, and record the angles (A) of the two angled portions 63 (see FIG. 1) of the sample relative to the lateral axis of the folded sample to the nearest 0.1 degrees. Repeat this procedure for 10 substantially similar absorbent article samples. Average together the 20 individual Folded Crotch Angle (A) measurements and report the value nearest 0.1 degrees.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
   a central lateral axis;
   a central longitudinal axis;
   a liquid permeable topsheet;
   a liquid impermeable backsheet;
   an absorbent core positioned at least partially intermediate the liquid permeable topsheet and the liquid impermeable backsheet;
   a first waist region;
   a second waist region;
   a crotch region extending intermediate the first waist region and the second waist region;
   an outer cover material joined to the backsheet and forming a portion of a garment-facing surface of the absorbent article;
   a pair of leg cuffs;
   a pair of crotch narrowing joints in the crotch region; and
   a fully removable fastening member comprising:
      a first surface;
      a second surface opposite to the first surface;
      a first end;
      a second end opposite to the first end;
      a first fastener on the first surface and positioned proximate to the first end; and
      a second fastener on the first surface and positioned proximate to the second end; wherein the fully removable fastening member has a slot or aperture defined therethrough, and wherein the slot aperture is positioned intermediate the first fastener and the second fastener; and
   a discrete wetness guard in the first waist region or the second waist region, wherein the wetness guard forms a portion of a wearer-facing surface of the absorbent article.

2. The absorbent article of claim 1, wherein the wetness guard comprises a laminate comprising:
   a first liquid impermeable layer facing the topsheet; and
   a liquid permeable layer forming a portion of the wearer-facing surface.

3. The absorbent article of claim 1, wherein the wetness guard comprises a hydrophilic nonwoven material and is free of a film.

4. The absorbent article of claim 1, wherein the wetness guard is in the first waist region, comprising a second wetness guard in the second waist region, and wherein the second wetness guard forms a portion of the wearer-facing surface of the absorbent article.

5. The absorbent article of claim 1, wherein the first fastener comprises a first plurality of hooks configured to engage the outer cover material, and wherein the second fastener comprises a second plurality of hooks configured to engage the outer cover material.

6. The absorbent article of claim 1, wherein the absorbent article has a folded crotch width of less than about 35 mm, according to the Folded Crotch Width Test herein.

7. The absorbent article of claim 1 comprising a first waist edge in the first waist region and a second waist edge in the second waist region, and wherein the first waist edge or the second waist edge has a first umbilical cord notch defined therein.

8. The absorbent article of claim 1, comprising a first waist edge in the first waist region and a second waist edge in the second waist region, and wherein the first waist edge or the second waist edge comprises a first umbilical cord projection.

9. The absorbent article of claim 1, wherein the topsheet comprises a plurality of apertures, comprising an acquisition layer positioned at least partially intermediate the topsheet and the absorbent core.

10. The absorbent article of claim 1, wherein the outer cover material has an Opacity in the range of about 5% to about 30%, according to the Opacity Test herein, and wherein the backsheet has an Opacity in the range of about 15% to about 70%, according to the Opacity Test herein.

11. The absorbent article of claim 1, wherein the absorbent core comprises an absorbent material, wherein the absorbent material has a first width, in a direction parallel to the central lateral axis, in the first waist region, wherein the absorbent material has a second width, in the direction parallel to the central lateral axis, in the second waist region, wherein the absorbent material has a third width, in the direction parallel to the central lateral axis, in the crotch region, and wherein the first width and the second width are greater than the third width.

12. The absorbent article of claim 1, wherein the fastening member comprises:
   a first nonwoven material forming a portion of the first surface;
   a second nonwoven material forming a portion of the second surface; and
   an elastic material positioned at least partially between the first nonwoven material and the second nonwoven material.

13. The absorbent article of claim 1, wherein the pair of crotch narrowing joints each comprise a bond positioned between a portion of the backsheet and a portion of the leg cuffs.

14. The absorbent article of claim 1, wherein the outer cover material or the backsheet comprises a first graphic in the first waist region, wherein the outer cover material or the backsheet comprises a second graphic in the second waist region, and wherein the first and second graphics are mirror images of each other, relative to the central lateral axis, to indicate reversibility of the absorbent article to a caregiver.

15. The absorbent article of claim 1, wherein the wetness guard is a discrete component, wherein a first portion of the first wetness guard is joined to the leg cuffs and/or the topsheet proximate to the first end edge of the absorbent article, wherein a second portion of the first wetness guard is joined to the leg cuffs and/or the topsheet proximate to the first side edge of the absorbent article, and wherein a third portion of the first wetness guard is joined to the leg cuffs and/or the topsheet proximate to the second side edge of the absorbent article.

16. The absorbent article of claim 1, wherein the first wetness guard has a first end positioned proximate to the first end edge of the absorbent article, wherein the first wetness guard has a second end positioned intermediate the first end edge of the absorbent article and the central lateral axis, and wherein the second end of the first wetness guard has at least a portion that is free of attachment with the topsheet.

17. A kit comprising:
  the absorbent article of claim 1; and
  an insert configured to be positioned on the wearer-facing surface of the absorbent article, wherein the insert comprises a grasp tab extending therefrom.

18. A package comprising a plurality of the absorbent articles of claim 1.

19. An absorbent article comprising:
  a central lateral axis;
  a central longitudinal axis;
  a liquid permeable topsheet;
  a liquid impermeable backsheet;
  an absorbent core positioned at least partially intermediate the liquid permeable topsheet and the liquid impermeable backsheet;
  a first waist region;
  a second waist region;
  a crotch region extending intermediate the first waist region and the second waist region;
  an outer cover material joined to the backsheet and forming a portion of a garment-facing surface of the absorbent article;
  a pair of leg cuffs;
  a pair of crotch narrowing joints in the crotch region; and
  a fully removable fastening member comprising:
    a first surface;
    a second surface opposite to the first surface;
    a first end;
    a second end; and wherein the fully removable fastening member has a slot or aperture defined therethrough, and wherein the slot aperture is positioned intermediate the first fastener and the second fastener opposite to the first end;
    a first fastener on the first surface and positioned proximate to the first end; and
    a second fastener on the first surface and positioned proximate to the second end.

* * * * *